United States Patent
Lee et al.

(10) Patent No.: US 9,352,158 B2
(45) Date of Patent: *May 31, 2016

(54) HEURISTIC SAFETY NET FOR TRANSITIONING CONFIGURATIONS IN A NEURAL STIMULATION SYSTEM

(71) Applicant: BOSTON SCIENTIFIC NEUROMODULATION CORPORATION, Valencia, CA (US)

(72) Inventors: Dongchul Lee, Agua Dulce, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/487,907

(22) Filed: Sep. 16, 2014

(65) Prior Publication Data

US 2015/0005848 A1 Jan. 1, 2015

Related U.S. Application Data

(63) Continuation of application No. 13/849,375, filed on Mar. 22, 2013, now Pat. No. 8,868,198.

(60) Provisional application No. 61/614,853, filed on Mar. 23, 2012.

(51) Int. Cl.
*A61N 1/372* (2006.01)
*A61N 1/36* (2006.01)
*A61N 1/05* (2006.01)

(52) U.S. Cl.
CPC .......... *A61N 1/36185* (2013.01); *A61N 1/0551* (2013.01); *A61N 1/36142* (2013.01); *A61N 1/37211* (2013.01); *A61N 1/37247* (2013.01); *A61N 1/37264* (2013.01)

(58) Field of Classification Search
CPC ............ A61N 1/36185; A61N 1/0551; A61N 1/36142; A61N 1/37211; A61N 1/37247; A61N 1/37264
USPC ......................................................... 607/59
See application file for complete search history.

(56) References Cited

U.S. PATENT DOCUMENTS 6,516,227 B1 2/2003 Meadows et al.
6,587,724 B2 7/2003 Mann
(Continued)

FOREIGN PATENT DOCUMENTS

EP 2827942 A2 1/2015
JP 2008526299 A 7/2008
(Continued)

OTHER PUBLICATIONS

U.S. Appl. No. 61/452,965, Neurostimulation System for Defining a Generalized Ideal Multipole Configuration, Inventor: Dongchul Lee, et al., filing date: Mar. 15, 2011.
(Continued)

*Primary Examiner* — Carl H Layno
*Assistant Examiner* — Erin M Piateski
(74) *Attorney, Agent, or Firm* — Schwegman Lundberg & Woessner, P.A.

(57) ABSTRACT

A system and method using a plurality of electrodes. An immediate virtual multipole is defined, an immediate electrode configuration emulating the immediate virtual multipole is defined, electrical energy is conveyed to the electrodes in accordance with the immediate electrode configuration, a new virtual multipole is defined by changing a parameter of the immediate virtual multipole by a step size, a new electrode configuration that emulates the new virtual multipole is defined, a difference value as a function of the immediate virtual multipole and the new virtual multipole is computed, the different value is compared to a limit value, electrical energy is conveyed to the electrodes in accordance with the new electrode configuration if the difference value does not exceed the limit value, and the absolute value of the step size is decreased to create a new step size if the difference value does exceed the limit value.

27 Claims, 22 Drawing Sheets

(56) References Cited

U.S. PATENT DOCUMENTS

| | | | |
|---|---|---|---|
| 6,895,280 | B2 | 5/2005 | Meadows et al. |
| 6,993,384 | B2 | 1/2006 | Bradley et al. |
| 8,868,198 | B2 * | 10/2014 | Lee et al. .................. 607/59 |
| 8,909,350 | B2 | 12/2014 | Lee |
| 8,918,185 | B2 | 12/2014 | Lee et al. |
| 2003/0040676 | A1 | 2/2003 | Prentice et al. |
| 2005/0203588 | A1 | 9/2005 | King |
| 2006/0229687 | A1 | 10/2006 | Goetz et al. |
| 2007/0049988 | A1 | 3/2007 | Carbunaru et al. |
| 2007/0239228 | A1 | 10/2007 | Bradley |
| 2007/0265679 | A1 | 11/2007 | Bradley et al. |
| 2008/0004674 | A1 | 1/2008 | King et al. |
| 2008/0004675 | A1 | 1/2008 | King et al. |
| 2008/0015563 | A1 | 1/2008 | Hoey et al. |
| 2008/0154341 | A1 | 6/2008 | McIntyre et al. |
| 2008/0183256 | A1 | 7/2008 | Keacher |
| 2009/0024184 | A1 | 1/2009 | Sun et al. |
| 2009/0054947 | A1 | 2/2009 | Bourn et al. |
| 2009/0118787 | A1 | 5/2009 | Moffitt et al. |
| 2009/0228070 | A1 | 9/2009 | Goetz et al. |
| 2009/0240302 | A1 | 9/2009 | Woods et al. |
| 2009/0287272 | A1 | 11/2009 | Kokones et al. |
| 2009/0287279 | A1 | 11/2009 | Parramon et al. |
| 2010/0010566 | A1 | 1/2010 | Thacker et al. |
| 2010/0121409 | A1 | 5/2010 | Kothandaraman et al. |
| 2010/0137943 | A1 | 6/2010 | Zhu |
| 2010/0268298 | A1 | 10/2010 | Moffitt et al. |
| 2011/0060386 | A1 | 3/2011 | Woods et al. |
| 2011/0064240 | A1 | 3/2011 | Litvak et al. |
| 2011/0106215 | A1 | 5/2011 | Moffitt |
| 2011/0257707 | A1 | 10/2011 | Kothandaraman |
| 2011/0319965 | A1 | 12/2011 | Fridman et al. |
| 2012/0016439 | A1 | 1/2012 | Alataris et al. |
| 2012/0022615 | A1 | 1/2012 | Goetz et al. |
| 2012/0029597 | A1 | 2/2012 | Keacher |
| 2012/0239115 | A1 | 9/2012 | Lee |
| 2013/0116751 | A1 | 5/2013 | Moffitt et al. |
| 2013/0253610 | A1 | 9/2013 | Lee et al. |
| 2013/0253611 | A1 | 9/2013 | Lee et al. |
| 2015/0073502 | A1 | 3/2015 | Lee et al. |

FOREIGN PATENT DOCUMENTS

| | | |
|---|---|---|
| JP | 2015513948 A | 5/2015 |
| WO | WO-2013142837 A3 | 9/2013 |

OTHER PUBLICATIONS

U.S. Appl. No. 61/576,924, Seamless Integration of Different Programming Modes for a Neurostimulator Programming System, Inventor: Sridhar Kothandaraman, et al., filing date: Dec. 16, 2011.

PCT International Search Report for PCT/US2013/033593, Applicant: Boston Scientific Neuromodulation Corporation, Form PCT/ISA/210 and 220, dated Sep. 19, 2013 (7pages).

PCT Written Opinion of the International Search Authority for PCT/US2013/033593, Applicant: Boston Scientific Neuromodulation Corporation, Form PCT/ISA/237, dated Sep. 19, 2013 (8pages).

"U.S. Appl. No. 13/849,375, Non Final Office Action mailed Jan. 16, 2014", 13 pgs.

"U.S. Appl. No. 13/849,375, Notice of Allowance mailed Jul. 1, 2014", 8 pgs.

"U.S. Appl. No. 13/849,375, Preliminary Amendment filed Mar. 22, 2013", 8 pgs.

"U.S. Appl. No. 13/849,375, Response filed Apr. 15, 2014 to Non Final Office Action mailed Jan. 16, 2014", 5 pgs.

"U.S. Appl. No. 13/849,384, Advisory Action mailed Jul. 21, 2014", 3 pgs.

"U.S. Appl. No. 13/849,384, Final Office Action mailed May 19, 2014", 16 pgs.

"U.S. Appl. No. 13/849,384, Non Final Office Action mailed Feb. 10, 2014", 15 pgs.

"U.S. Appl. No. 13/849,384, Notice of Allowance mailed Oct. 1, 2014", 5 pgs.

"U.S. Appl. No. 13/849,384, Preliminary Amendment filed Mar. 22, 2014", 14 pgs.

"U.S. Appl. No. 13/849,384, Response filed Mar. 10, 2014 to Non Final Office Action mailed Feb. 10, 2014", 21 pgs.

"U.S. Appl. No. 13/849,384, Response filed Jul. 8, 2014 to Final Office Action mailed May 19, 2014", 7 pgs.

"U.S. Appl. No. 13/849,384, Response filed Sep. 15, 2014 to Advisory Action mailed Jul. 21, 2014", 17 pgs.

"U.S. Appl. No. 14/543,696, Non Final Office Action mailed Sep. 10, 2015", 17 pgs.

"Australian Application Serial No. 2013234883, First Examiner Report mailed Nov. 16, 2014", 3 pgs.

"European Application Serial No. 13716906.6, European Search Report mailed Sep. 19, 2013", 5 pgs.

"European Application Serial No. 13716906.6, Office Action mailed Oct. 28, 2014", 1 pg.

"European Application Serial No. 13716906.6, Office Action mailed Nov. 28, 2014", 1 pg.

"International Application Serial No. PCT/US2013/033593, International Preliminary Report on Patentability mailed Oct. 2, 2014", 10 pgs.

"Japanese Application Serial No. 2015-501943, Office Action mailed Sep. 24, 2015", 3 pgs.

* cited by examiner

HEURISTIC SAFETY NET FOR TRANSITIONING CONFIGURATIONS IN A NEURAL STIMULATION SYSTEM

RELATED APPLICATION DATA

The present application is a continuation of U.S. patent application Ser. No. 13/849,375, filed Mar. 22, 2013, now U.S. Pat. No. 8,868,198, which claims the benefit under 35 U.S.C. §119 to U.S. Provisional Patent Application Ser. No. 61/614,853, filed Mar. 23, 2012. The foregoing applications are each hereby incorporated by reference into the present application in their entirety.

FIELD OF THE INVENTION

The present disclosure relates to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses provided through the electrode array. Each electrode configuration, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means, and subsequently to program the neurostimulator with the optimum stimulation parameter set or sets. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

To determine the stimulation parameters to be programmed, the Bionic Navigator® may be operated by a clinician in one of three modes: (a) a manual programming mode to manually select the cathodic current and anodic current flowing through the electrodes; (b) an electronic trolling ("e-troll") mode to quickly sweep the electrode array using a limited number of electrode configurations to gradually move a cathode in bipolar stimulation; and (c) a Navigation programming mode to fine tune and optimize stimulation coverage for patient comfort using a wide number of electrode configurations. These three modes allow the clinician to determine the most efficient stimulation parameter sets for a given patient.

In the manual programming mode, the clinician directly selects individual electrodes and the current magnitude and polarity to be applied to each selected electrode. In the navigation and e-troll programming modes, the Bionic Navigator® semi-automatically transitions between different electrode configurations to electrically "steer" the current along the implanted leads in real-time (e.g., using a joystick or joystick-like controls) in a systematic manner, thereby allowing the clinician to determine the most efficacious stimulation parameter sets that can then be stored and eventually combined into stimulation programs. In the context of SCS, current steering is typically either performed in a rostro-caudal direction (i.e., along the axis of the spinal cord) or a medial-lateral direction (i.e., perpendicular to the axis of the spinal cord).

The navigation and e-troll programming modes differ in part in the way in which the clinician changes electrode configurations from one configuration to another. E-troll programming mode utilizes a technique known as "panning," which shifts a pre-defined electrode configuration down the sequence of electrodes without changing the basic form of the electrode configuration. Navigation programming mode utilizes a technique known as "weaving," which moves the anode or anodes around the cathode, while slowly progressing the cathode down the sequence of electrodes. The e-troll and Navigation programming modes may have different clinical uses (e.g., finding the "sweet spot" in the case of panning, or shaping the electrical field around the cathode in the case of weaving).

In one novel current steering method, described in U.S. patent application Ser. No. 12/938,282, entitled "System and Method for Mapping Arbitrary Electric Fields to Pre-existing Lead Electrodes," which is expressly incorporated herein by reference, a stimulation target in the form of a virtual pole (e.g., a virtual bipole or tripole) is defined and the stimulation parameters, including the fractionalized current values on each of the electrodes, are computationally determined in a manner that emulates these virtual poles. It can be appreciated that current steering can be implemented by moving the virtual poles about the leads, such that the appropriate fractionalized current values for the electrodes are computed for each of the various positions of the virtual pole. As a result, the current steering can be implemented using an arbitrary number and arrangement of electrodes, thereby solving the aforedescribed problems.

When performing current steering, it is desirable that the transitions in the resulting electrical field be as smooth as possible, such that the patient does not experience drastic changes in the stimulation regimen, which may either result in an uncomfortable or even painful sensation caused by overstimulation or a sudden loss of therapy caused by understimulation. In the context of SCS, cathodic electrodes dominate the stimulation effect, and thus, the overstimulation may occur when there is a significant increase in the percentage of current on certain cathodic electrodes, and understimulation may occur when there is a significant decrease of the percentage of current on certain cathodic electrodes. There, thus, remains a need to ensure that the transitions between electrode configurations be as smooth as possible during current steering.

SUMMARY OF THE INVENTION

In accordance with the present inventions, a system for an electrical neurostimulator coupled to a plurality of electrodes and a method of operating the same to provide therapy to a patient is provided. The system comprises telemetry circuitry configured for communicating with the electrical neurostimulator, and a controller/processor. The system may further comprises a user interface configured for receiving a user input. The system may also comprise a housing containing the telemetry circuitry and the controller/processor. This system and method may implement one or more of several techniques for smoothly transitioning electrical stimulation energy between different electrode configurations.

One technique comprises (a) defining an immediate virtual multipole, (b) defining an immediate electrode configuration (e.g., a fractionalized combination) that emulates the immediate virtual multipole, (c) instructing the electrical neurostimulator via the telemetry circuitry to convey electrical energy to the plurality of electrodes in accordance with the immediate electrode configuration, (d) defining a new virtual multipole by changing a parameter (e.g., a location, focus, and/or upper anode percentage) of the immediate virtual multipole by a step size (which may be either positive or negative), and (e) defining a new electrode configuration (e.g., a fractionalized combination) that emulates the new virtual multipole.

This technique further comprises (f) computing a difference value as a function of the immediate virtual multipole and the new virtual multipole. In one embodiment, the difference value is a function of the immediate electrode configuration and the new electrode configuration. For example, the difference value may comprise a change in a cathodic current on an individual one of the electrodes, a change in an anodic current on an individual one of the electrodes, a total change in cathodic current on the electrodes, or a total change in anodic current on the electrodes. In another embodiment, the difference value is a function of one of an electrical field, absolute potential, current density, an activating function, and a total net driving function that is derived from the immediate virtual multipole and the new virtual multipole. In still another embodiment, the difference value is a displacement between one pole of the immediate virtual multipole and a corresponding pole of the new virtual multipole.

This technique further comprises (g) comparing the difference value to a limit value, (h) instructing the electrical neurostimulator to convey electrical energy to the plurality of electrodes in accordance with the new electrode configuration if the difference value does not exceed the limit value; and (i) not instructing the electrical neurostimulator to convey electrical energy to the plurality of electrodes, decreasing the absolute value of the step size to create a new step size, and repeating steps (d)-(i) for the new step size if the difference value exceeds the limit value.

In one embodiment, this technique comprises (d) defining the new virtual multipole by changing another parameter of the immediate virtual multipole by another step size, and (i) decreasing the absolute value of the other step size to create another new step size, and repeating steps (d)-(i) for the new step size and the other new step size if the difference value exceeds the limit value. In another embodiment, the technique comprises (f) computing another difference value as another function of the immediate virtual multipole and the new virtual multipole, (g) comparing the other difference value to another limit value, (h) instructing the electrical neurostimulator to convey the electrical energy to the plurality of electrodes in accordance with the new set of stimulation parameters if neither the difference value exceeds the limit value nor the other difference value exceeds the other limit value, and (i) decreasing the absolute value of the step size to create the new step size and repeating steps (d)-(i) for the new step size if either the difference value exceeds the limit value or the other difference value exceeds the other limit value.

Another technique comprises defining an immediate electrode configuration, conveying electrical energy to the plurality of electrodes in accordance with the immediate electrode configuration, defining a final electrode configuration, defining a series of intermediate electrode configurations using a heuristic set of rules based on the immediate electrode configuration and the final electrode configuration, instructing the electrical neurostimulator to convey electrical energy to the plurality of electrodes in accordance with the series of intermediate electrode configurations, and instructing the electrical neurostimulator to convey electrical energy to the plurality of electrodes in accordance with the subsequent electrode configuration.

The series of intermediate electrode configurations may be defined by repeatedly defining a next intermediate electrode configuration based on an immediate previously defined electrode configuration and the final electrode configuration until the next intermediate electrode configuration matches the final electrode configuration. In this case, the heuristic set of rules may comprise limiting shifting of the anodic and/or cathodic current from the immediate previously defined electrode configuration to the next intermediate electrode configuration based on one or more of the following: a maximum change in a cathodic current on an individual one of the electrodes, a maximum change in an anodic current on an individual one of the electrodes, a total maximum change in cathodic current on the electrodes, and a total maximum change in anodic current on the electrodes.

In one embodiment, each of the electrodes has an electrical current transition between the immediate previously defined electrode configuration and the final electrode configuration that is one of the following: no current change transition, a cathodic current increase transition, a cathodic current decrease transition, a cathodic current decrease/anodic current increase transition, an anodic current increase transition, an anodic current decrease transition, and an anodic current decrease/cathodic current increase transition, and wherein the controller/processor is configured for applying the heuristic set of rules to the electrical current transitions to define the next intermediate electrode configuration.

The shift in the electrical current will depend on the transition between the immediate previously defined electrode configuration and the final electrode configuration.

For example, if one of the electrodes has a cathodic decrease transition, and another one of the electrodes has a cathodic increase transition, the heuristic set of rules may shift the cathodic current from the one electrode to the other one electrode.

As another example, if one of the electrodes has an anodic current decrease/cathodic current increase transition, the heuristic set of rules may shift the anodic current from the one electrode to another one of the electrodes, which may, e.g., have an anodic current increase transition, or may have no current change transition or an anodic current decrease transition. At least one more of the electrodes may have an anodic current decrease/cathodic current increase transition, and the one electrode may have a greater cathodic current than does the at least one more electrode for the final electrode configuration.

As still another example, if one of the electrodes has a cathodic current decrease/anodic current increase transition, the heuristic set of rules may comprise shifting cathodic current from the one electrode to another one of the electrodes, which may, e.g., have a cathodic current increase transition, or may have no current change transition or a cathodic current decrease transition. The other one electrode may have a cathodic current decrease/anodic current increase transition, and the other one electrode may have the greatest cathodic current for the final electrode configuration.

As yet another example, if one of the electrodes has an anodic decrease transition, and another one of the electrodes has an anodic increase transition, the heuristic set of rules may shift the anodic current from the one electrode to the other one electrode.

The heuristic rules can be combined into a series of inquiries that prioritizes the electrodes for which the electrical current will be shifted.

For example, the heuristic set of rules may comprise determining whether there exists a first electrode pairing having a cathodic current increase transition and a cathodic current decrease transition, and shifting cathodic current from the electrode having the cathodic current decrease transition to the electrode having the cathodic current increase transition if the first electrode pairing is determined to exist; determining whether there exists a second electrode pairing having a cathodic current increase transition and a cathodic current decrease/anodic current increase transition, and shifting cathodic current from the electrode having the cathodic current decrease/anodic current increase transition to the electrode having the cathodic current increase transition if the second electrode pairing is determined to exist; determining whether there exists a third electrode pairing having an anodic current increase transition and an anodic current decrease transition, and shifting anodic current from the electrode having the anodic current decrease transition to the electrode having the anodic current increase transition if the third electrode pairing is determined to exist; and determining whether there exists a fourth electrode pairing having an anodic current increase transition and an anodic current decrease/cathodic current increase transition, and shifting anodic current from the electrode having the anodic current decrease/cathodic current increase transition to the electrode having the anodic current increase transition if the fourth electrode pairing is determined to exist.

If none of the first, second, third, and fourth electrode pairings exists, the heuristic set of rules may comprise determining whether there exists a first electrode having an anodic current decrease/cathodic current increase transition and whether there exists a second electrode having either a no current change transition or an anodic current decrease transition. If the first and second electrode exists, the heuristic set of rules shifts anodic current from the first electrode to the second electrode. If either the first electrode or the second electrode does not exist, the heuristic set of rules comprises shifting cathodic current from an electrode having a cathodic current decrease/anodic current increase transition to an electrode having either a no current change transition or a cathodic current decrease transition.

The heuristic set of rules may further comprise determining whether all of the electrodes either have a cathodic current decrease/anodic current increase transition or an anodic current decrease/cathodic current decrease transition. If all of the electrodes either have a cathodic current decrease/anodic current increase transition or an anodic current decrease/cathodic current decrease transition, the heuristic set of rules further comprises determining whether there exists multiple electrodes each having an anodic current decrease/cathodic current increase transition, and if the multiple electrodes exist, determining which one of the multiple electrodes has the greatest cathodic current for the final electrode configuration, and shifting anodic current from the one electrode to another electrode. The heuristic set of rules further comprises, if the multiple electrodes do not exist, determining one electrode having the greatest cathodic current for the previous intermediate electrode configuration, and shifting cathodic current from any electrode having cathodic current for the previous intermediate electrode configuration to the one electrode.

Other and further aspects and features of the disclosure will be evident from reading the following detailed description of the preferred embodiments, which are intended to illustrate, not limit, the disclosure.

BRIEF DESCRIPTION OF THE DRAWINGS

The drawings illustrate the design and utility of preferred embodiments of the present disclosure, in which similar elements are referred to by common reference numerals. In order to better appreciate how the above-recited and other advantages and objects of the present disclosure are obtained, a more particular description of the present disclosure briefly described above will be rendered by reference to specific embodiments thereof, which are illustrated in the accompanying drawings. Understanding that these drawings depict only typical embodiments of the disclosure and are not therefore to be considered limiting of its scope, the disclosure will be described and explained with additional specificity and detail through the use of the accompanying drawings in which.

DETAILED DESCRIPTION OF THE EMBODIMENTS

The description that follows relates to spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
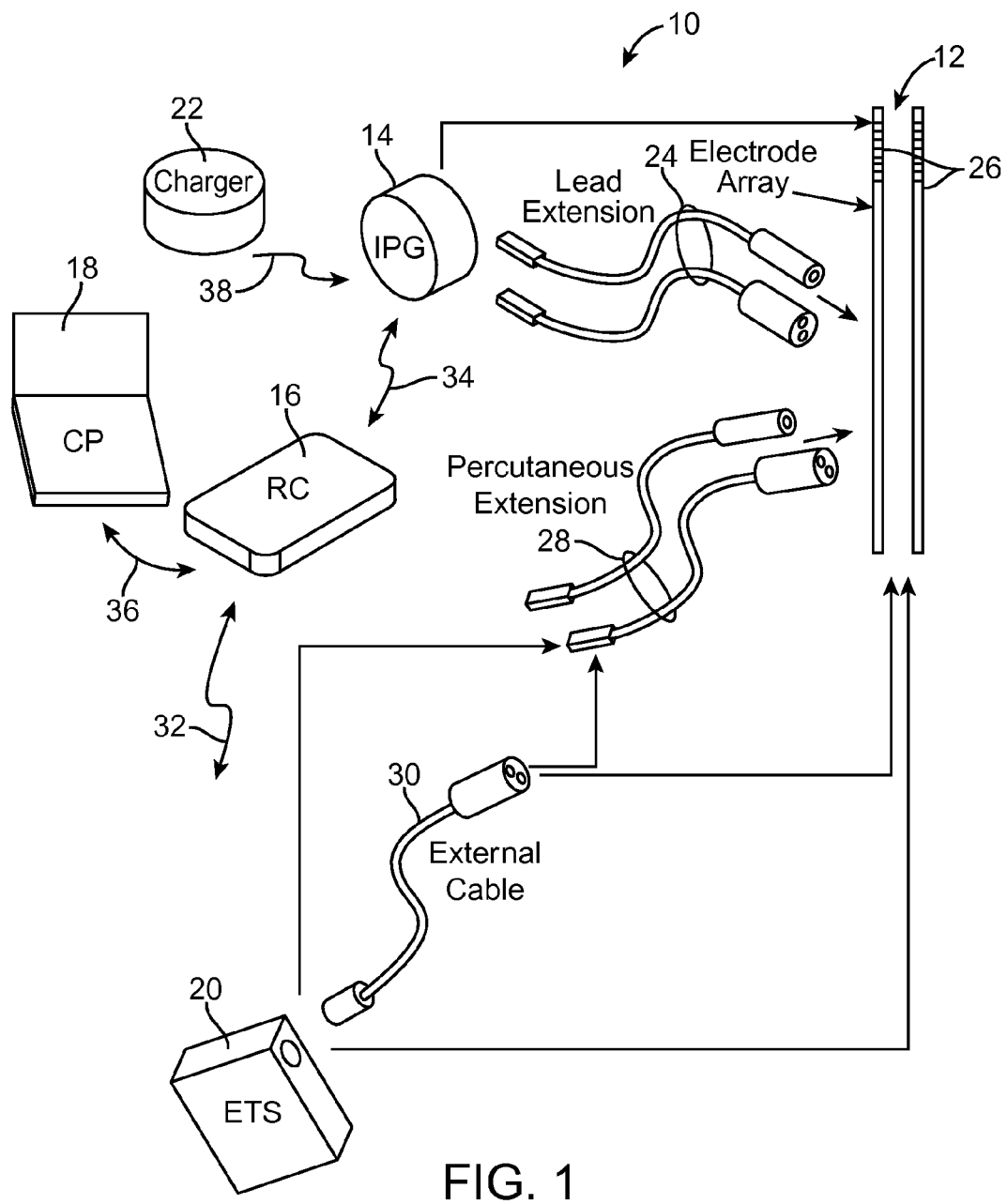
FIG. 1 is a plan view of a Spinal cord Stimulation (SCS) system constructed in accordance with one embodiment of the present disclosure.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead in can be used in place of one or more of the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
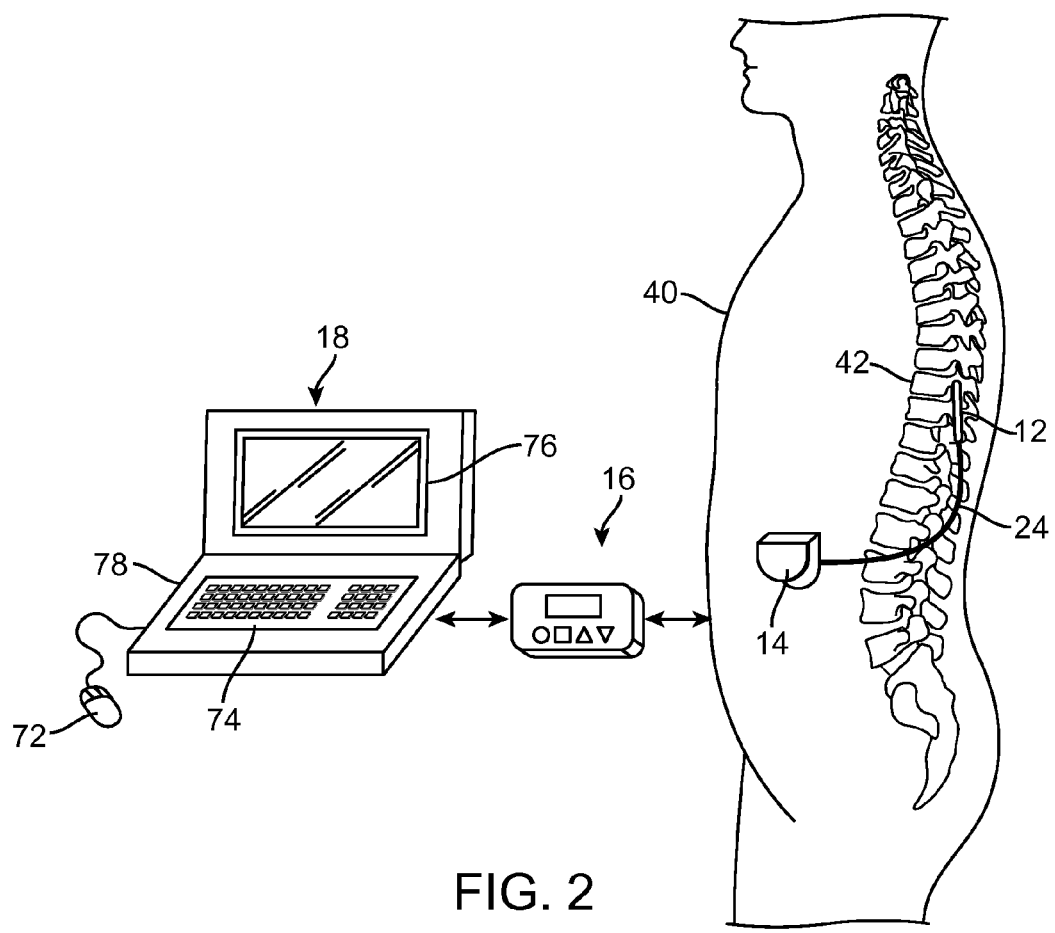
FIG. 2 is a perspective view of the arrangement of the SCS system of FIG. 1 with respect to a patient.

As shown in FIG. 2, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 3:
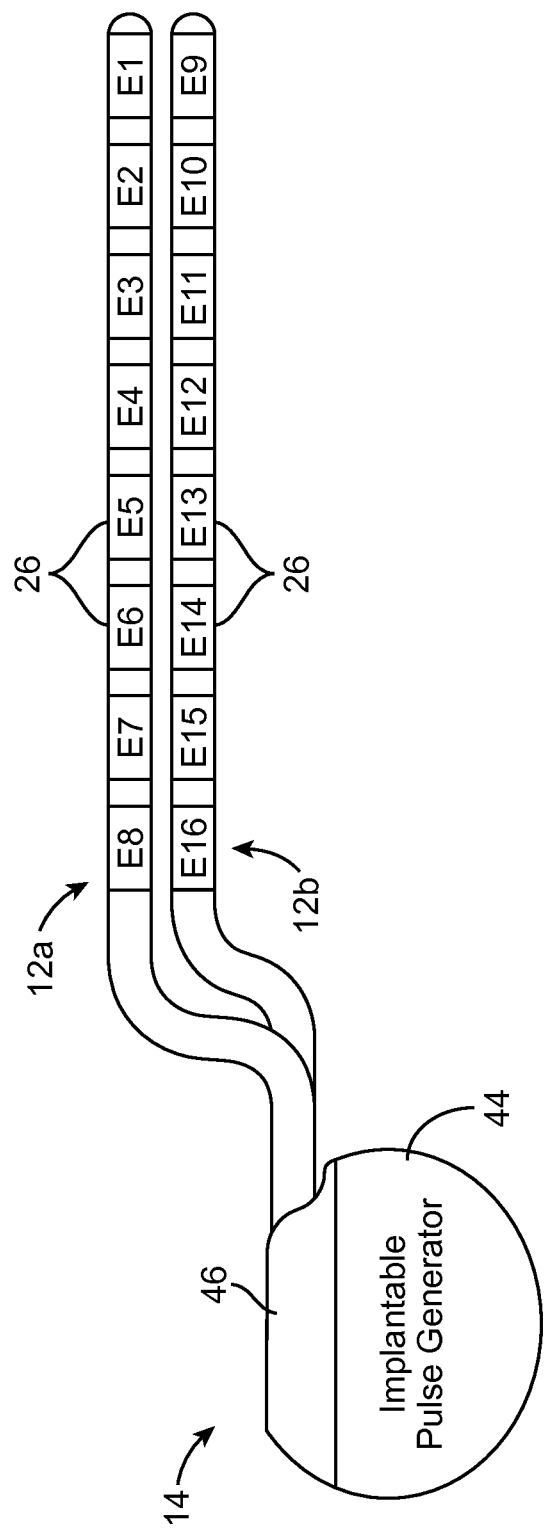
FIG. 3 is a profile view of an implantable pulse generator (IPG) and percutaneous leads used in the SCS system of FIG. 1.

Referring now to FIG. 3, the external features of the neurostimulation leads 12 and the IPG 14 will be briefly described. One of the neurostimulation leads 12a has eight electrodes 26 (labeled E1-E8), and the other stimulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neurostimulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode configurations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
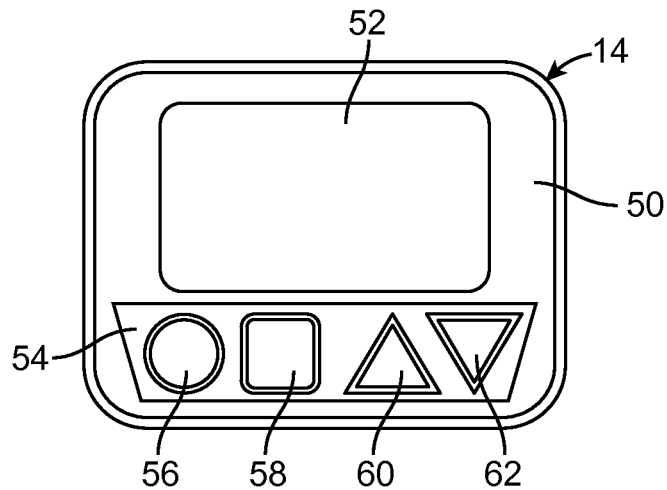
FIG. 4 is front view of a remote control (RC) used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
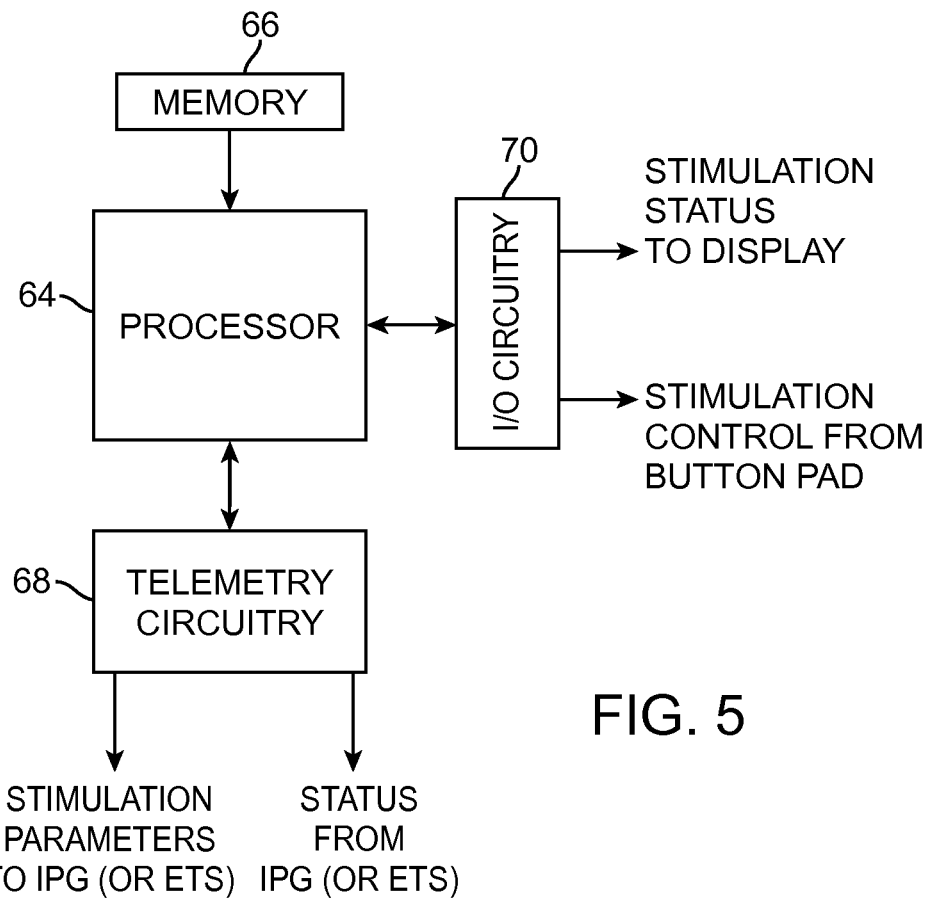
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets, input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode configurations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc., can be used to manipulate graphical objects on the display screen 76. In alternative embodiments, the display screen 76 takes the form of a digitizer touch screen, which may either passive or active. If passive, the display screen 76 includes detection circuitry that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked.

Figure 6:
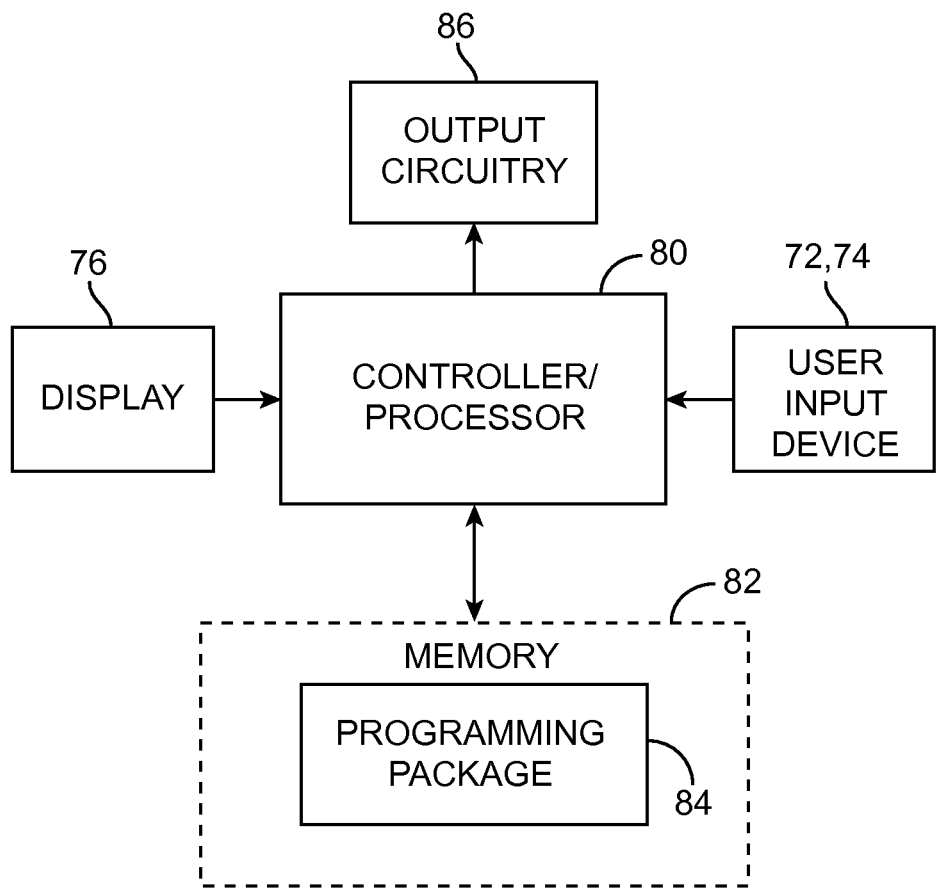
FIG. 6 is a block diagram of the internal components of a clinician's programmer (CP) used in the SCS system of FIG. 1.

As shown in FIG. 6, the CP 18 generally includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16. Notably, while the controller/processor 80 is shown in FIG. 6 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor.

Execution of the programming package 84 by the controller/processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a user interface that conveniently allows a user to program the IPG 14 using different programming modes, and in the illustrated embodiment, three programming modes: a manual programming mode, an e-troll programming mode, and a Navigation programming mode.

Figure 7:
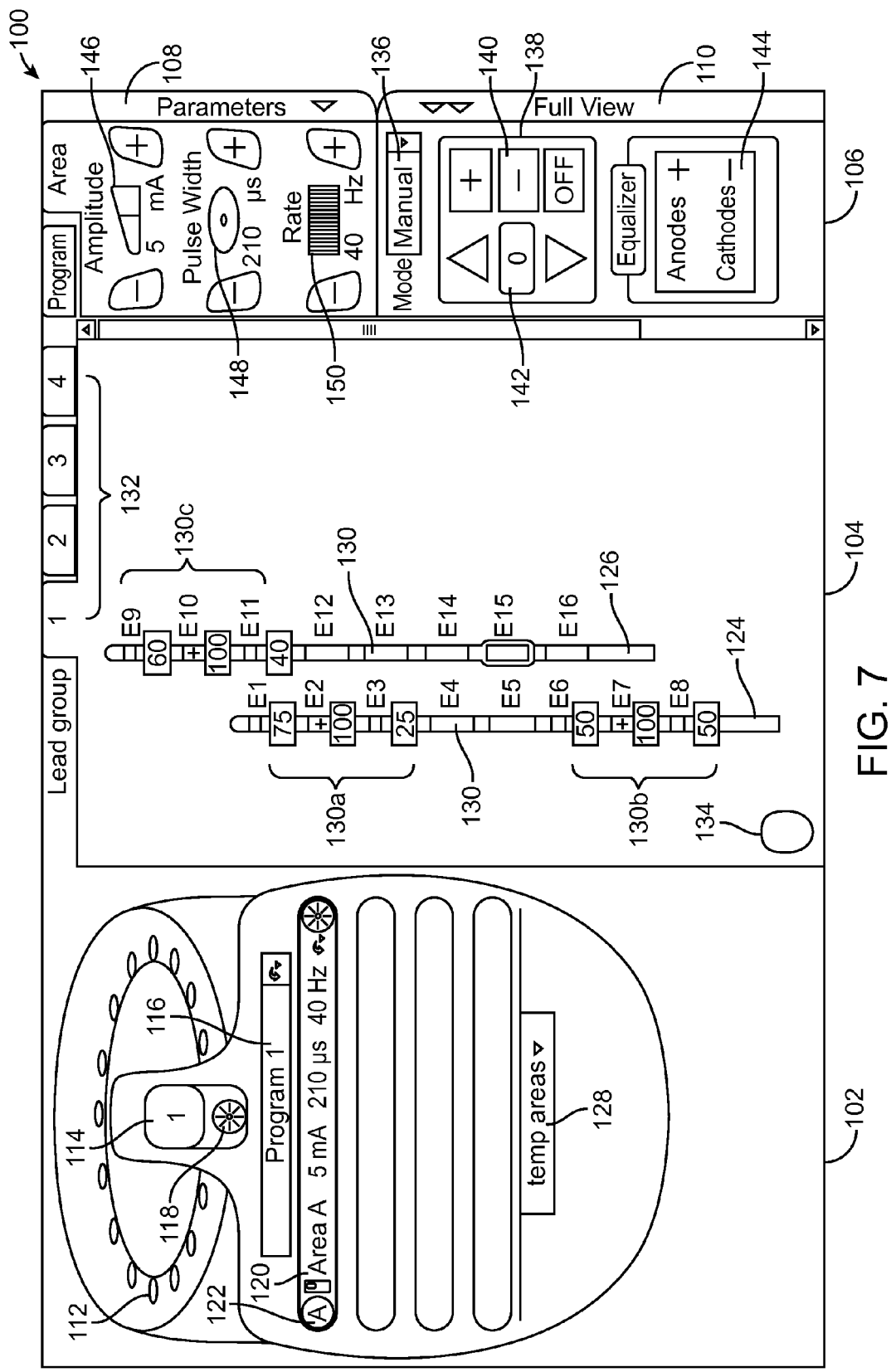
FIG. 7 is a plan view of a user interface of the CP of FIG. 6 for programming the IPG of FIG. 3 in a manual mode.

Referring now to FIG. 7, a graphical user interface (GUI) 100 that can be generated by the CP 18 to allow a user to program the IPG 14 will be described. In the illustrated embodiment, the GUI 100 comprises three panel: a program selection panel 102, a lead display panel 104, and an electrical parameter adjustment panel 106. Some embodiments of the GUI 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about programs and areas that have been, or may be, defined for the IPG 14. A plurality of programs may be displayed in carousel 112. In the illustrated embodiment, sixteen programs may be defined, but program 1 is the only one currently defined, as shown by the "1" in field 114. Other embodiments may use a carousel or other techniques for displaying available programs with different numbers or arrangements of available program slots.

Each program may be named, as indicated by the name field 116. A stimulation on/off button 118 allows turning the currently active program on or off. When the active program is on, stimulation parameter sets will be generated in the CP 18 and transmitted to the RC 16. Up to four program areas 120 may be defined, allowing a program to control stimulation of multiple areas. Each program area 120 may separately control stimulation of electrodes in the patient, and may be separately turned on or off. Each of the program areas 120 may be labeled with a label 122 that may be used as a marker on the graphical leads 124 and 126, as described below. A number of temporary areas 128 may be used for temporary storage of area information by copying a program area 120 into a temporary area 128 or copying a temporary area 128 into a program area 120. This allows copying a program area 120 from one of the four slots to another slot via one of the temporary areas 128. Other embodiments may also allow copying one of the program areas 120 into another one of the program areas 120 directly. Individual programs may be copied to other slots in the carousel 112 or deleted as desired.

Turning now to the lead display panel 104, graphical leads 124 and 126 are illustrated with eight graphical electrodes 130 each (labeled electrodes E1-E8 for lead 124 and electrodes E9-E16 for lead 126). Other numbers of leads and electrodes per lead may be displayed as desired. In an implanted system using other numbers of electrodes, that number of electrodes may be shown in lead display panel 104. Up to four groups of leads may be viewed by selecting one of the lead group tabs 132. In addition, an icon 134 representing the case 44 of the IPG 14 is displayed in the lead display panel 104. In addition to allocating current to any of the electrodes of graphical leads 124 and 126, current may be allocated to the case 44 as an electrode.

Each of the electrodes 130 of the leads 124 and 126 may be individually selected, allowing the clinician to set the polarity and the magnitude of the current allocated to that electrode 130. In the illustrated embodiment, electrode E15 is currently selected. Electrical current has been allocated to three groups of electrodes respectively corresponding to three programming areas. Electrode group 130a illustrates a single cathode at electrode E2 to which is allocated 100% of the cathodic current and two anodes at electrodes E1 and E3 to which are allocated 25% and 75% of the anodic current, respectively. Electrode group 130b illustrates a single anode at electrode E7 to which is allocated 100% of the cathodic current and two anodes at electrodes E6 and E8 to which are allocated 50% and 50% of the anodic current, respectively. Electrode group 130c illustrates a single anode at electrode E10 to which is allocated 100% of the cathodic current and two anodes at electrodes E9 and E11 to which are allocated 60% and 40% of the anodic current, respectively.

The parameters adjustment panel 106 includes a pull-down programming mode field 136 that allows the user to switch between the manual programming mode, the e-troll programming mode, and the Navigation programming mode. As shown in FIG. 7, the manual programming mode has been selected. In the manual programming mode, each of the electrodes 130 of the graphical leads 124 and 126, as well as the graphical case 132, may be individually selected, allowing the clinician to set the polarity (cathode or anode) and the magnitude of the current (percentage) allocated to that electrode 134 using graphical controls located in the amplitude/polarity area 138. In particular, a graphical polarity control 140 located in the area 138 includes a "+" icon, a "−" icon, and an "OFF" icon, which can be respectively actuated to toggle the selected electrode 134 between a positive polarization (anode), a negative polarization (cathode), and an off-state. An amplitude control 142 in the area 138 includes an arrow that can be actuated to decrease the magnitude of the fractionalized current of the selected electrode 134, and an arrow that can be actuated to increase the magnitude of the fractionalized current of the selected electrode 134. The amplitude control 142 also includes a display area that indicates the adjusted magnitude of the fractionalized current for the selected electrode 134. Amplitude control 142 is preferably disabled if no electrode is visible and selected in the lead display panel 104.

Figure 8:
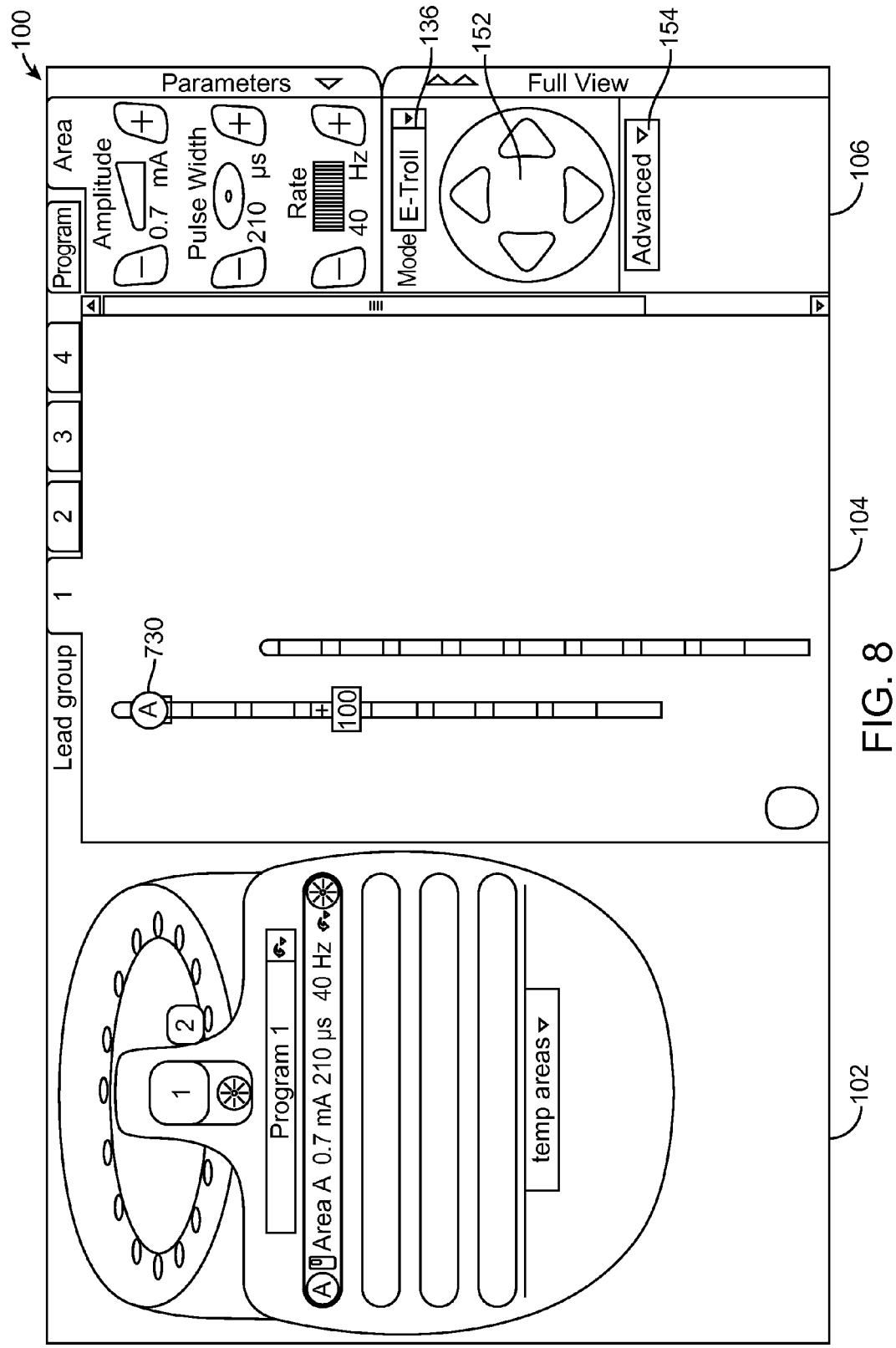
FIG. 8 is a plan view of a user interface of the CP of FIG. 6 for programming the IPG of FIG. 3 in an e-troll mode.
Figure 9:
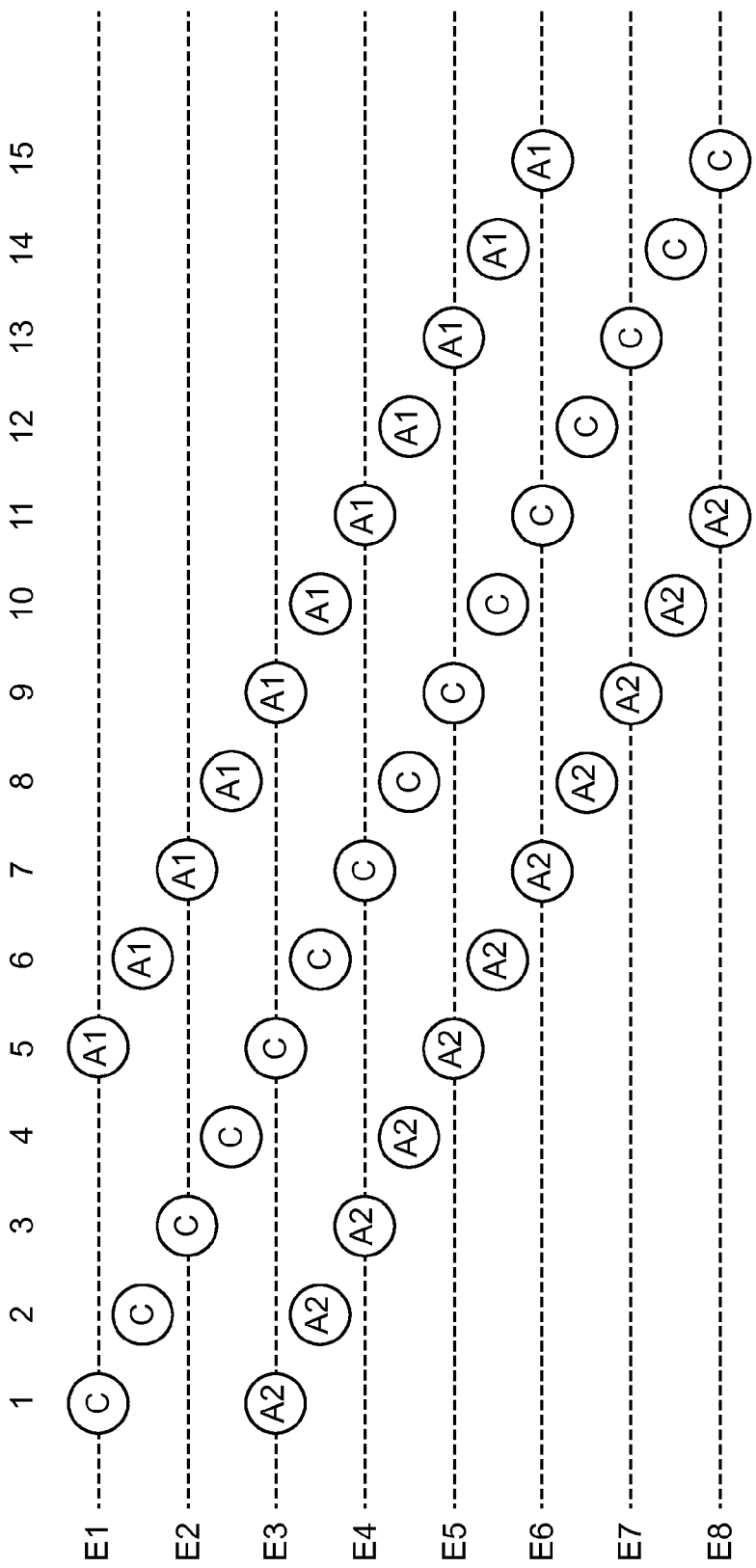
FIG. 9 is a panned sequence of a multipole used by the e-troll mode of FIG. 8 to program the IPG of FIG. 3.

The parameters adjustment panel 106, when the manual programming mode is selected, also includes an equalization control 144 that can be actuated to automatically equalize current allocation to all electrodes of a polarity selected by respective "Anode +" and "Cathode −" icons. The parameters adjustment panel 106 also includes a pulse amplitude adjustment control 150 (expressed in milliamperes (mA)), a pulse width adjustment control 148 (expressed in microseconds (μs)), and a pulse rate adjustment control 146 (expressed in Hertz (Hz)), which are displayed in all three of the programming modes. Each of the controls 146, 148, 150 includes a first arrow that can be actuated to decrease the value of the respective stimulation parameter and a second arrow that can be actuated to increase the value of the respective stimulation parameter. Each of the controls 146, 148, 150 also includes a display area for displaying the currently selected parameter. In the illustrated embodiment, a pulse amplitude of 5 mA, a pulse width of 210 μs, a pulse rate of 60 Hz have been selected. The controls 146, 148, 150 are also displayed in As shown in FIG. 8, the e-troll programming mode has been selected. In this mode, the electrodes 130 illustrated in the lead display panel 104 that were individually selectable and configurable in manual programming mode are used for display only and are not directly selectable or controllable. The parameter selection panel 106 includes a steering array of arrows 152 that allows steering the electrical current up, down, left, or right. In the illustrated embodiment, the electrical current is steered by panning a virtual multipole (i.e., the virtual multipole is moved relative to the actual electrodes 26 without changing the basic configuration (focus (F) and upper anode percentage (UAP)) of the virtual multipole), and computing the electrical amplitude values needed for the actual electrodes 26 to emulate the virtual multipole. For example, as shown in FIG. 9, a series of virtual multipoles, and in this case, tripoles and bipoles, are sequentially defined in accordance with a panned current steering technique over a plurality of dashed lines representing available electrode positions in the electrode array 26.

In the illustrated embodiment, all of the virtual tripoles are symmetrical in that the virtual anodes are equally spaced from the central virtual cathode. The nominal virtual multipoles can also be considered wide tripole/bipoles in that the virtual anode(s) are spaced a relatively large distance from the cathode (in this case, by two electrodes). Between the ends of the electrode array 26, a virtual tripole is panned along the electrode array 26 (i.e., the LGF value is maintained as the virtual cathode is shifted along the electrode array 26). However, as either of the outer virtual anodes of the virtual tripole abuts the last electrode in the array, a virtual bipole is utilized (upper virtual bipole at the top of the electrode array 26, and a lower virtual bipole at the bottom of the electrode array 26). The virtual bipole may then be panned along the electrode array 26 (i.e., the LGF value is maintained as the virtual cathode is shifted along the electrode array 26).

Figure 10:
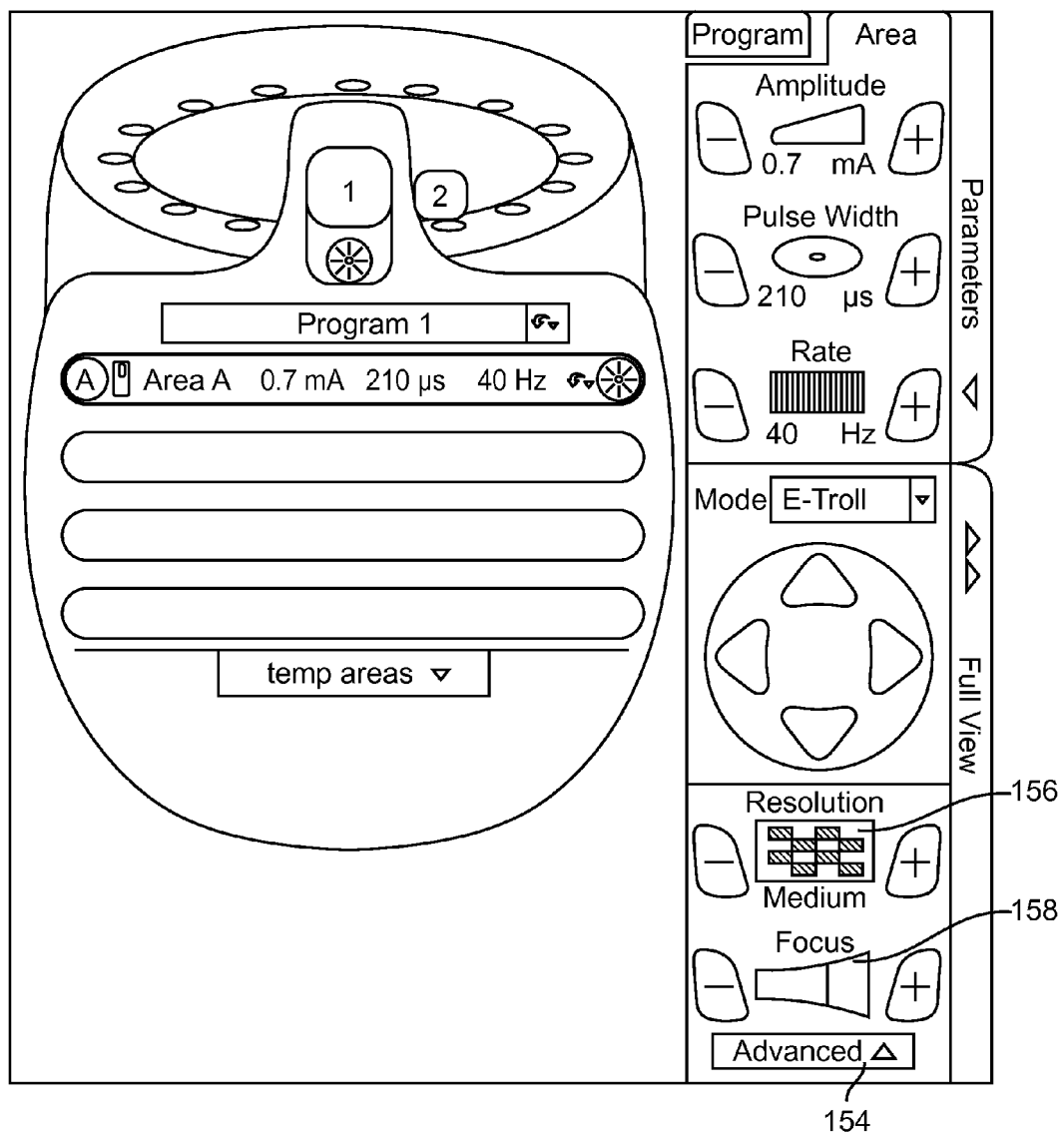
FIG. 10 is a plan view of the user interface of FIG. 8, particularly showing the expansion of the Advanced Tab into resolution and focus controls.

In the e-troll programming mode, the parameter adjustment panel 106 also includes an advanced tab 154, which when actuated, hides the lead display panel 104 and provides access to a resolution control 156 and a focus control 158, as shown in FIG. 10.

The resolution control 156 allows changing the stimulation adjustment resolution. In one embodiment, three possible settings of Fine, Medium, and Coarse may be chosen. The resolution control 156 has a "+" icon and a "−" icon that can be used to adjust the resolution. The resolution control 156 also includes a display element that graphically displays the current resolution level. When the resolution is set to Fine, each change caused by use of the steering arrows 152 makes less of a change to the electrode configuration than when the resolution is set to Medium or Coarse. For example, panning of the virtual multipole with a Coarse resolution may displace the virtual multipole relative to the electrode array 26 in steps equivalent to 10% of the electrode spacing, whereas panning of the virtual multipole with a Fine resolution may move the virtual multipole relative to the electrode array 26 in steps equivalent to 1% of the electrode spacing.

The focus control 158 allows changing the stimulation focus by displacing the anode(s) and cathode of the virtual multipole toward each other to increase the focus, or displacing the anode(s) and cathode of the virtual multipole away from each other to decrease the focus. The focus control 158 has a "+" icon and a "−" icon that can be used to adjust the focus. The focus control 158 also includes a display element that graphically displays the current focus level.

Figure 11:
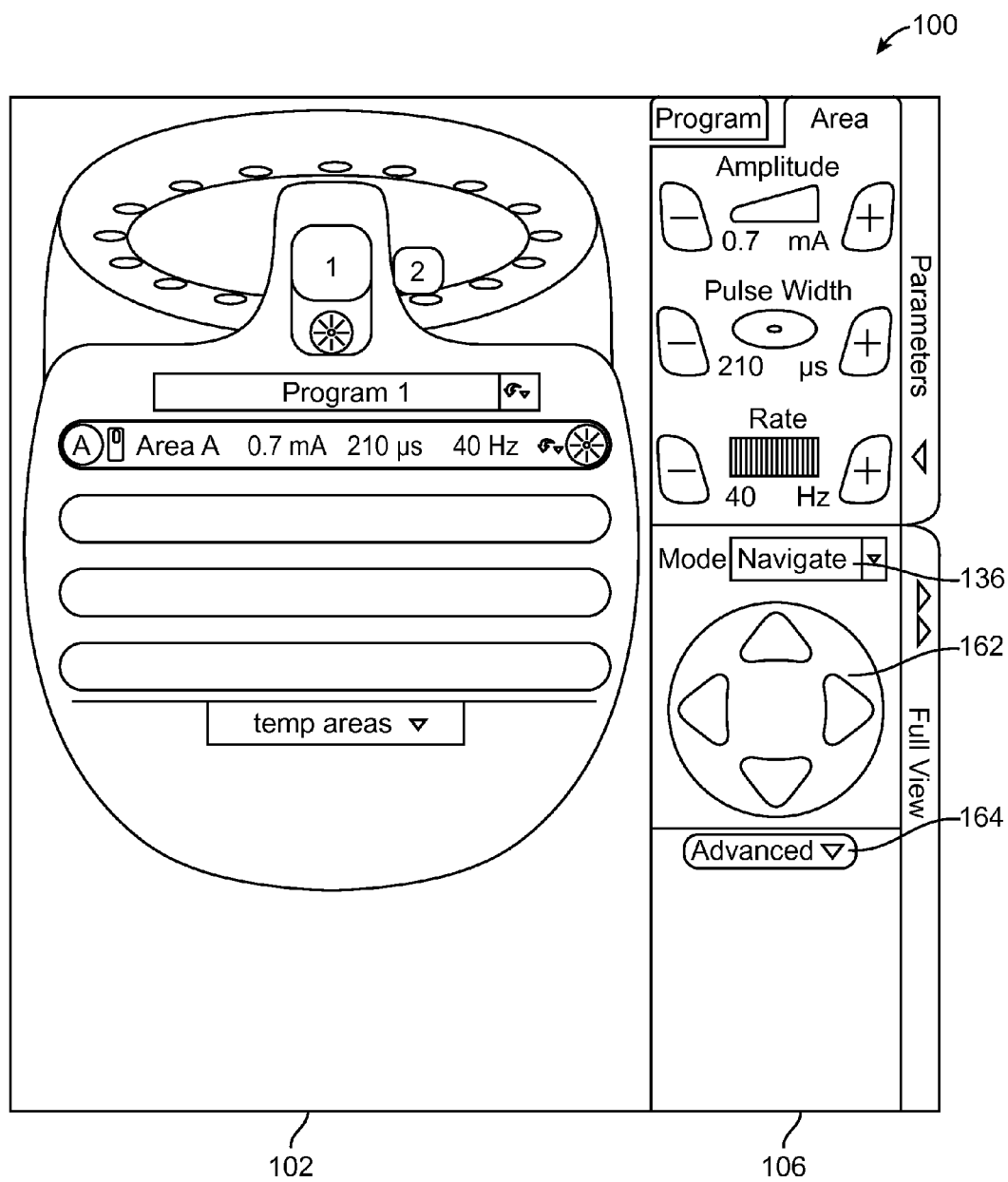
FIG. 11 is a plan view of a user interface of the CP of FIG. 6 for programming the IPG of FIG. 3 in a Navigation mode.

As shown in FIG. 11, the Navigation programming mode has been selected. As in the e-troll programming mode, in the Navigation programming mode, the electrodes illustrated in the lead display panel 104 that were individually selectable and configurable in manual programming mode are used for display only and are not directly selectable or controllable. The parameter selection panel 106 includes a steering array of arrows 162 that allows steering the electrical current up, down, left, or right. In the illustrated embodiment, the electrical current is steered by weaving one or more anodes around the cathode of the virtual multipole as the cathode is displaced relative to the electrode array 26, and computing the electrical amplitude values needed for the electrodes 26 to emulate the virtual multipole.

Figure 12:
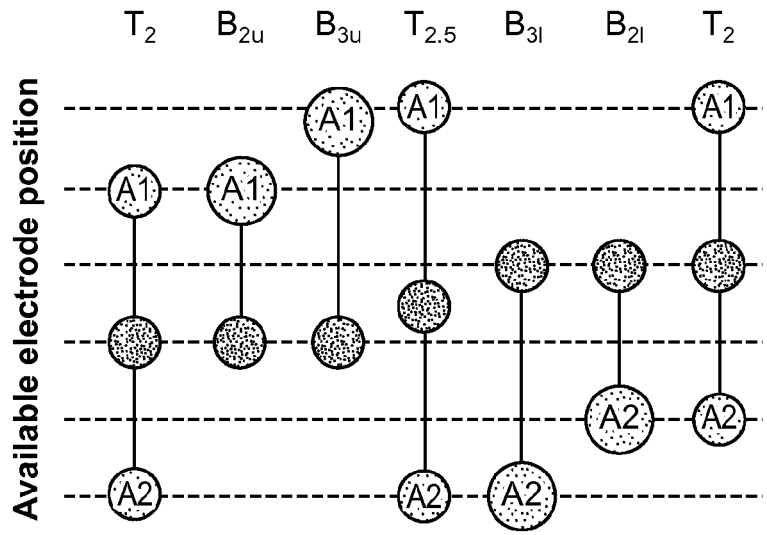
FIG. 12 is a sequence of different virtual multipoles used by the Navigation mode of FIG. 10 to program the IPG of FIG. 3.

For example, as shown in FIG. 12, a series of virtual multipoles are sequentially defined in accordance with a weaved current steering technique over a plurality of dashed lines representing available electrode positions in the electrode array 26. Each illustrated multipole has a designator indicating whether it is a tripole or bipole (T for tripole and B for bipole), a subscripted designator indicating the longitudinal focus (LGF) in terms of electrode separation, and, in the case of a bipole, a subscripted designator indicating the bipole is an upper bipole (u), meaning that the anode is above the cathode, or the bipole is a lower bipole (I), meaning that the anode is below the cathode.

In the embodiment illustrated in FIG. 12, the different virtual multipoles are sequentially defined in the following order: a narrow virtual tripole ($T_2$), a narrow upper virtual bipole ($B_{2u}$), a wide upper virtual bipole ($B_{3u}$), a wide virtual tripole ($T_{2.5}$), a wide lower virtual bipole ($B_{3l}$), a narrow lower virtual bipole ($B_{2l}$), and the narrow virtual tripole ($T_2$). For purposes of this specification, the terms "narrow" and "wide," when used together to define a virtual bipole or a virtual tripole in either the e-troll programming mode or the Navigation programming mode, are relative terms, and simply mean that the narrow bipole and/or narrow tripole have longitudinal focuses (LGFs) that are less than the longitudinal focuses (LGFs) of the wide bipole and/or wide tripole.

Figure 13:
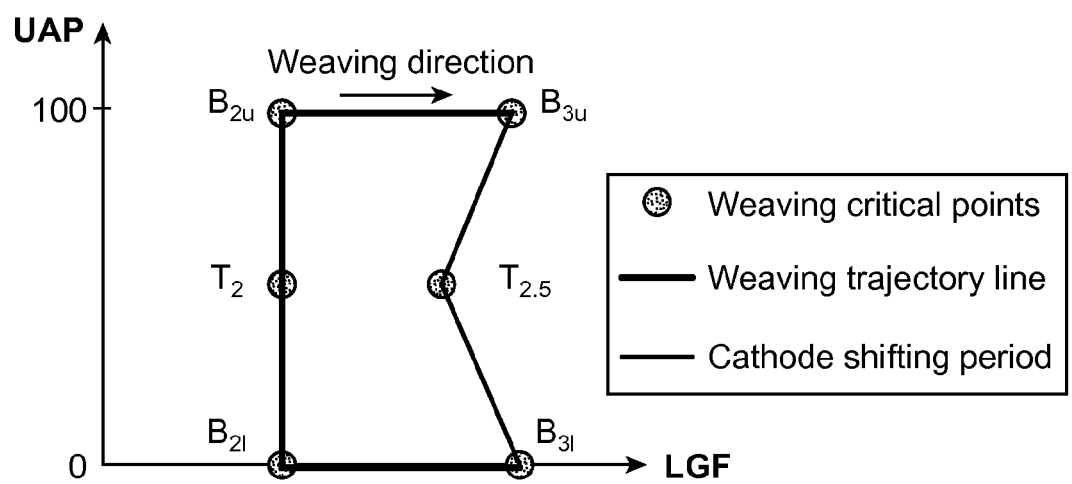
FIG. 13 is a plot illustrating a weaving space for the sequence of the multipoles illustrated in FIG. 12.

The virtual multipoles illustrated in FIG. 12 may be considered critical points between which the cathode position and longitudinal focus (LGF) are incrementally changed by mapping the sequences in a "weave space," defined by the longitudinal focus (LGF) and the upper anode percentage (UAP). As best shown in FIG. 13, the sequence of virtual multipoles is defined by a trajectory line sequentially connecting the critical points (representing by circles) that provides a continuous change in the virtual multipoles.

As can be seen from FIG. 13, the sequence beginning with the narrow virtual tripole ($T_2$) and ending with the narrow upper virtual bipole ($B_{2u}$) incrementally increases the upper anode percentage (UAP) while maintaining the longitudinal focus (LGF). The sequence beginning with the narrow upper virtual bipole ($B_{2u}$) and ending with the wide upper virtual bipole ($B_{3u}$) maintains the upper anode percentage (UAP) while incrementally increasing the longitudinal focus (LGF). The sequence beginning with the wide upper virtual bipole ($B_{3u}$) and ending with the wide virtual tripole ($T_{2.5}$) incrementally decreases the upper anode percentage (UAP) while incrementally decreasing the longitudinal focus (LGF). The sequence beginning with the wide virtual tripole ($T_{2.5}$) and ending with the wide lower virtual bipole ($B_{3l}$) incrementally decreases the upper anode percentage (UAP) while incrementally increasing the longitudinal focus (LGF). The sequence beginning with the wide lower virtual bipole ($B_{3l}$) and ending with the narrow lower virtual bipole ($B_{2l}$) maintains the upper anode percentage (UAP) while incrementally decreasing the longitudinal focus (LGF). The sequence beginning with the narrow lower virtual bipole ($B_{2l}$) and ending with the narrow virtual tripole ($T_2$) incrementally increases the upper anode percentage (UAP) while maintaining the longitudinal focus (LGF).

Notably, the above-mentioned sequence maintains the same position of the virtual cathode relative to the electrode array 26 while transitioning through different types of virtual bipole/tripoles between the narrow virtual tripole ($T_2$) and the wide upper virtual bipole ($B_{3u}$), incrementally changes the position of the virtual cathode relative to the electrode array 26 in one direction (in this case, upward) between the wide upper virtual bipole ($B_{3u}$) and the wide lower virtual bipole ($B_{3l}$), and the maintains the same position of the virtual cathode relative to the electrode array 26 while transitioning through different types of virtual bipole/tripoles between the wide lower virtual bipole ($B_{3l}$) and the narrow virtual tripole ($T_2$). The sequence illustrated in FIG. 12 can be repeatedly cycled through, with the effect being that the virtual cathode is shifted upward by one electrode per each cycle. Further details discussing various weaved current steering techniques are described in U.S. Provisional Patent Application Ser. No. 61/452,965, entitled "Neurostimulation System for Defining a Generalized Virtual Multipole," which has previously been incorporated herein by reference.

In the Navigation programming mode, the parameter adjustment panel 106 also includes the previously described advanced tab 154, which when actuated, hides the lead display panel 104 provides access to the resolution control 156 and the focus control 158 in the same manner described above with respect to the e-troll programming mode in FIG. 10.

The resolution control 156 allows changing the stimulation adjustment resolution. In one embodiment, three possible settings of Fine, Medium, and Coarse may be chosen. When the resolution is set to Fine, each change caused by use of the steering arrows 162 makes less of a change to the electrode configuration than when the resolution is set to Medium or Coarse. In particular, depending on the resolution, different step sizes may be used transition between the virtual multipoles illustrated in FIG. 12. For example, if the resolution is set to be Fine, a fine resolution (10 steps per critical point transition) may be used to transition between the critical points where the cathode is not being shifted, and an even finer resolution (20 steps per critical point transition) may be used to transition between the critical points where the cathode is being shifted. If the resolution is set to be Coarse, a coarse resolution (5 steps per critical point transition) may be used to transition between all of the critical points.

The focus control 158 allows changing the stimulation focus by displacing the anode(s) and cathode of each of the virtual multipoles toward each other to increase the focus, or displacing the anode(s) and cathode of each of the virtual multipoles away from each other to decrease the focus.

The CP 18 may transition between different programming modes using techniques disclosed in U.S. Provisional Patent Application Ser. No. 61/576,924, entitled "Seamless Integration of Different Programming Modes for a Neurostimulator Programming System," which is expressly incorporated herein by reference.

Figure 14:
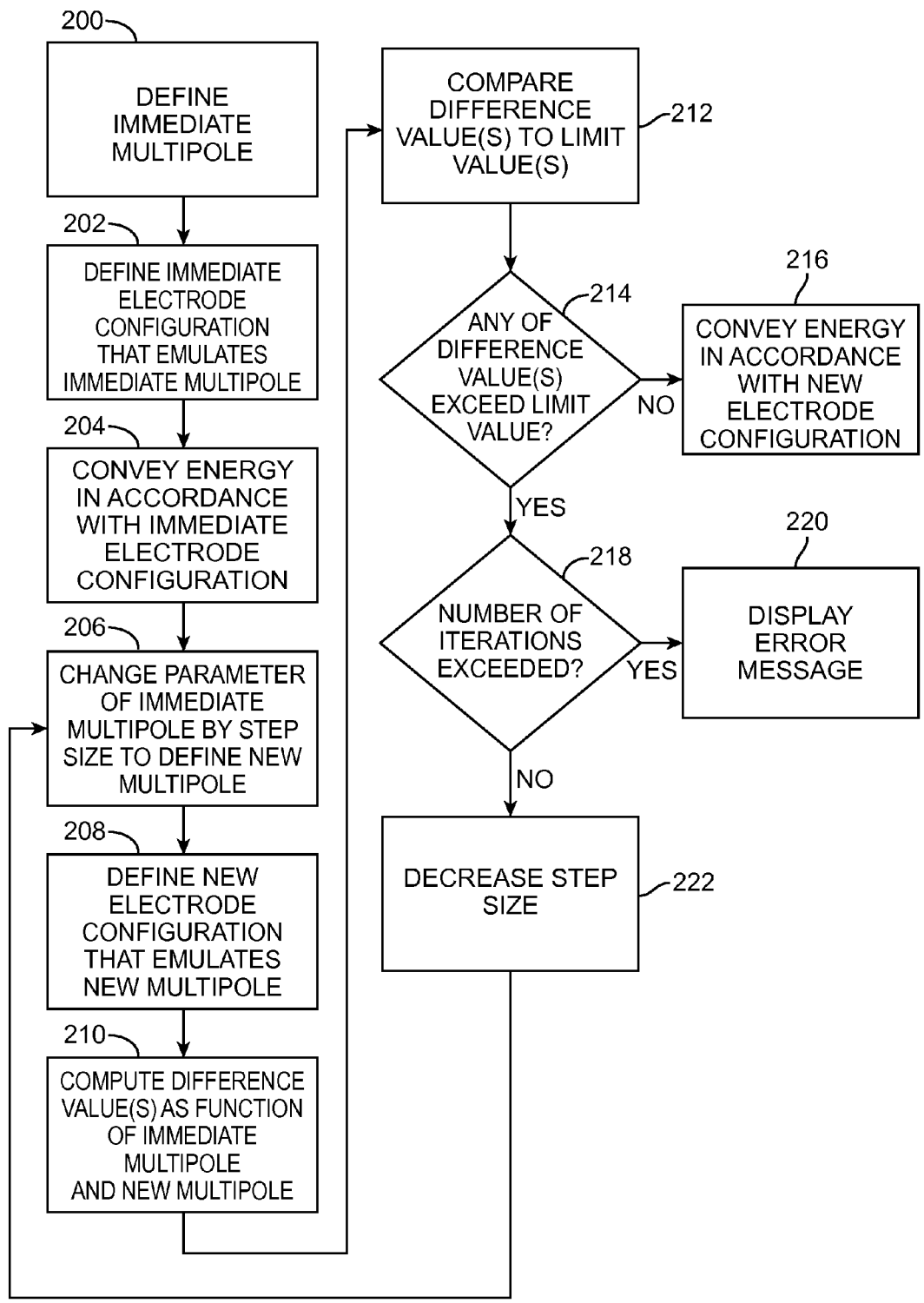
FIG. 14 is a flow chart illustrating one method used by the SCS system of FIG. 1 to steer electrical current in accordance with one set of heuristic rules.

As discussed in the background, it is desirable to steer the electrical current in a manner that transitions the resulting electrical field as smoothly as possible. To this end, the CP 18 utilizes a Heuristic Safety Net (HSN) that ensures that comfortable and efficacious therapy is maintained as each virtual multipole is transitioned to the next virtual multipole. Referring to FIG. 14, one method of using an HSN when steering current will now be described.

First, the CP 18 defines an immediate virtual multipole (step 200), defines a immediate fractionalized electrode configuration that emulates the immediate virtual multipole (step 202), and instructs the IPG 14 to convey electrical energy to the electrodes 26 in accordance with the immediate fractionalized electrode configuration (step 204). In response to actuation of any of the steering arrows in the GUI 100 (steering arrows 152 when in the E-troll programming mode or steering arrows 162 when in the Navigation programming mode), the CP 18 defines a new virtual multipole by changing a parameter of the immediate virtual multipole by a step size (step 206) and defines a new fractionalized electrode configuration that emulates the new virtual multipole (step 208). In the illustrated embodiment, the new virtual multipole can be computed in accordance with the equation: $X_{new}=X_{current}+\Delta X$ or $X_{new}=X_{current}-\Delta X$, where $X_{new}$ is the parameter of the new virtual multipole, $X_{current}$ is the parameter of the immediate virtual multipole, and $\Delta X$ is the step size. Thus, the parameter of the immediate virtual multipole can be either increased by the step size or decreased by the step size to generate the new virtual multipole.

The parameter may be, e.g., an x-y location of the virtual multipole (e.g., in the case where the virtual multipole is panned in the e-troll programming mode) or a focus or upper anode percentage (e.g., in the case where the virtual multipole is weaved in the Navigation programming mode). The step size(s) of the parameter may be adjusted, e.g., via the resolution control 156. In some cases, such as when in the Navigation programming mode, the CP 18 may define the new virtual multipole by respectively changing multiple parameters (e.g., the focus and upper anode percentage) of the immediate virtual multipole by a multiple of step sizes.

Next, the CP 18 computes one or more difference values as a function of the immediate virtual multipole and the new virtual multipole (step 210) and respectively compares the difference value(s) to one or more limit value(s) (step 212). In the illustrated embodiment, the difference value(s) is a function of the immediate fractionalized electrode configuration and the new fractionalized electrode configuration. In an alternative embodiment, the difference value(s) is a function of one or more of an electrical field, absolute potential, current density, an activating function, a total net driving function, etc. derived from the immediate virtual multipole and the new virtual multipole. In another alternative embodiment, the difference value may be a displacement between one pole (e.g., the virtual cathode) of the immediate virtual multipole and a corresponding pole of the new virtual multipole.

In the case where the difference value(s) is a function of the immediate fractionalized electrode configuration and the new fractionalized electrode configuration, the difference value(s) may be, e.g., a change in a fractionalized cathodic current on an individual one of the electrodes 26 (CI) (e.g., if the cathodic current on electrode E2 changes from 5% to 15%, the difference value will be 10%), a change in a fractionalized anodic current on an individual one of the electrodes 26 (AI) (e.g., if the anodic current on electrode E8 changes from 50% to 30%, the difference value will be 20%), a total fractionalized change in cathodic current on the electrodes 26 (CT) (e.g., if the cathodic current on electrode E1 changes from 10% to 20%, the cathodic current on electrode E2 changes from 30% to 20%, and the cathodic current on the remaining electrodes remains the same, the difference value will be 20%), and/or a total fractionalized change in anodic current on the electrodes 26 (AT) (e.g., if the anodic current on electrode E7 changes from 20% to 25%, and the anodic current on electrode E8 changes from 35% to 30%, and the anodic current on the remaining electrodes remains the same, the difference value will be 10%). The limit values may be, e.g., in the range of 5-50% for CI, 5-80% for AI, 10-90% for CT, and 10-90% for AT. In the illustrated embodiment, all of the electrodes 26 are considered when comparing the different value(s) to the respective limit value(s). In an alternative embodiment, less than all of the electrodes may be considered when comparing the different value(s) to the respective limit value(s).

Next, the CP 18 compares the difference value(s) to the respective limit value(s) (step 214). If none of the difference value(s) exceeds the respective limit value, the CP 18 instructs the IPG 14 to convey electrical energy to the electrodes 26 in accordance with the new fractionalized electrode configuration (step 216). If any of the different value(s) exceeds the respective limit value, the CP 18 does not instruct the IPG 14 to convey electrical energy to the electrodes 26, but instead determines whether the number of times the difference value(s) have been compared to the respective limit value(s) has exceeded a maximum number of iterations (e.g., in the range of 2-20 iterations) (step 218). If the maximum number of iterations has been exceeded, the CP 18 returns an error message to the user indicating such (step 220). If the maximum number of iterations has not been exceeded, the CP 18 decreases the absolute value of the step size to create a new step size (step 222), and then repeats steps 206-218 for the new step size. The absolute value of the step size can be decreased in accordance with the equation $\Delta X_{new}=\Delta X_{current}\cdot K$, where $\Delta X_{new}$ is the new step size, $\Delta X_{current}$ is the current step size, and K is a multiplication factor that is less than 1. In the case where multiple parameters are used to generate the new virtual multipole, all of the step sizes associated with these multiple parameters may be decreased.

Figure 15A:
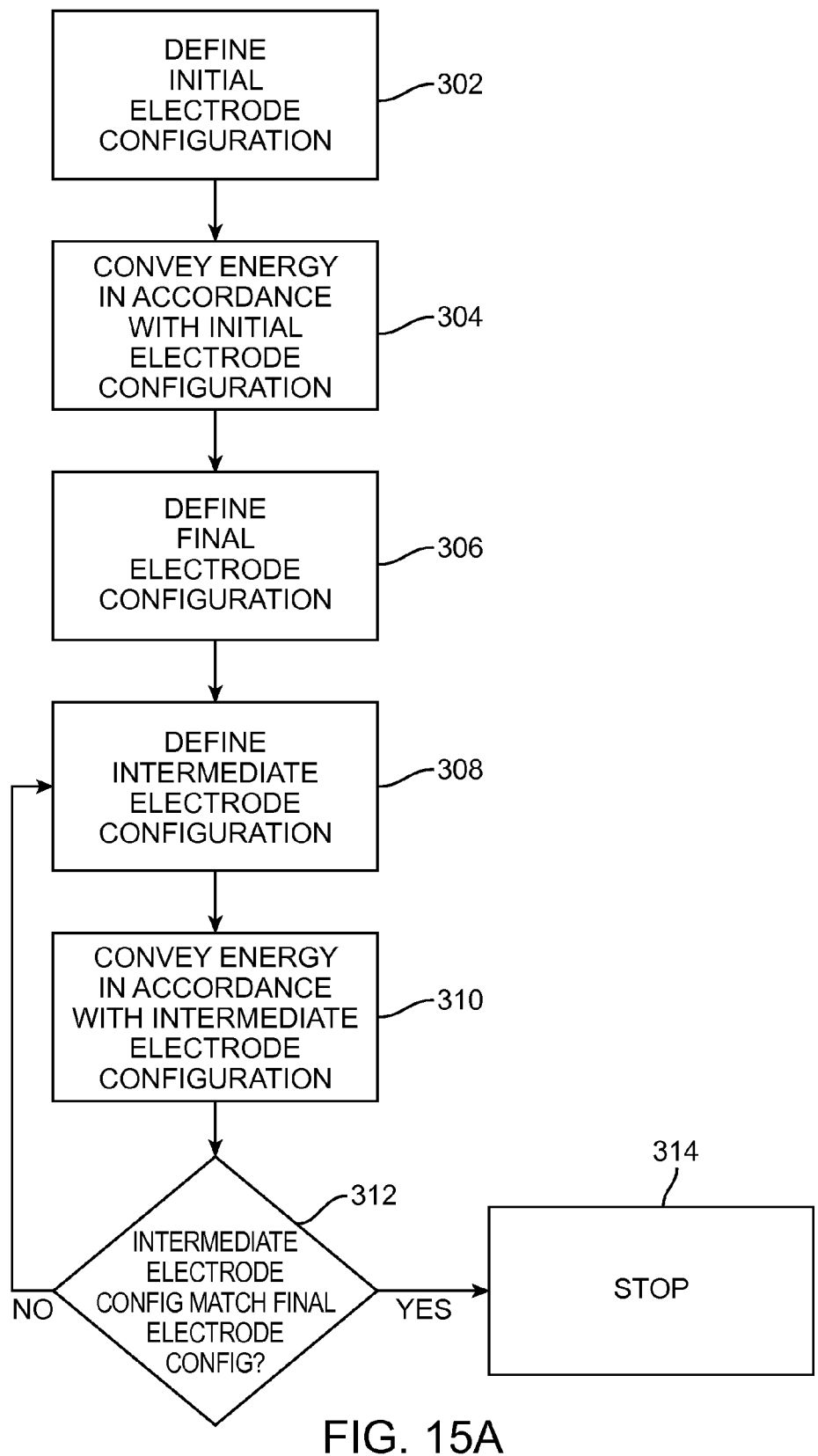
FIGS. 15A and 15B are flows charts illustrating another method used by the SCS system of FIG. 1 to steer electrical current in accordance with another set of heuristic rules.
Figure 15B:
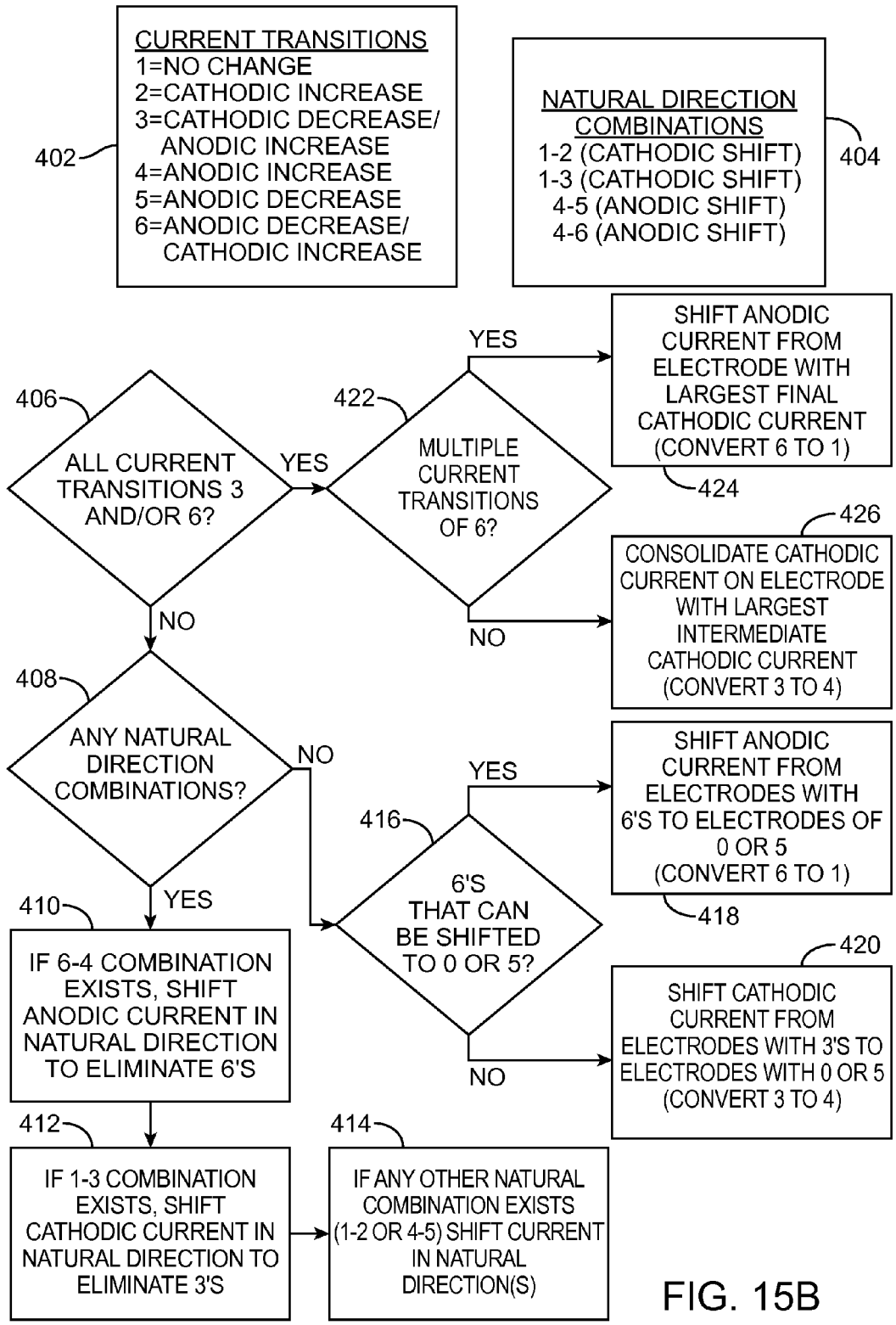

Referring to FIGS. 15A and 15B, another method of using an HSN when steering current will now be described. In this method, an HSN is employed to define and apply electrode configuration transitions between an immediate electrode configuration and a final electrode configuration. With reference first to FIG. 15A, the CP 18 defines an immediate (initial) electrode configuration, which may be a fractionalized electrode configuration as discussed above (step 302), and instructs the IPG 14 to convey electrical energy to the electrodes 26 in accordance with the immediate fractionalized electrode configuration (step 304).

In response to actuation of any of the steering arrows in the GUI 100 (steering arrows 152 when in the E-troll programming mode or steering arrows 162 when in the Navigation programming mode), the CP 18 defines a new (final) electrode configuration (step 306). To proceed from the existing initial configuration to the defined final configuration, the CP 18 defines a series of intermediate electrode configurations, and in particular, repeatedly defines a next intermediate electrode configuration based on an immediate previously defined electrode configuration and the final electrode configuration until the next intermediate electrode configuration matches the final electrode configuration (steps 308-314). In the illustrated embodiment, each next intermediate electrode configuration is defined by shifting anodic and/or cathodic current from the immediate previously defined electrode configuration to the next intermediate electrode configuration until the intermediate electrode configuration matches the final electrode configuration.

The heuristic set of rules limits shifting of the anodic and/or cathodic current from the immediate previously defined electrode configuration to the next intermediate electrode configuration based on, e.g., a maximum change in a fractionalized cathodic current on an individual one of the electrodes 26 (e.g., a maximum cathodic current change in the range of 5-50%), a maximum change in a fractionalized anodic current on an individual one of the electrodes 26 (e.g., a maximum anodic current change in the range of 5-80%), a total fractionalized change in cathodic current on the electrodes 26 (e.g., a maximum cathodic current change in the range of 10-90%), and a total fractionalized change in anodic current on the electrodes 26 (e.g., a maximum cathodic current change in the range of 10-90%). In the illustrated embodiment, all of the electrodes 26 are considered when comparing the different value(s) to the respective limit value(s). In an alternative embodiment, less than all of the electrodes may be considered when comparing the different value(s) to the respective limit value(s).

While considering the maximum current change limits discussed above, the CP 18 defines the next intermediate electrode configuration based on electrical current transitions between the electrodes of the immediate previously defined electrode configuration and the respective electrodes of the final electrode configuration. In this embodiment, a "transition" refers to a change in the electrical current being applied to individual electrodes in an electrode configuration. Thus, a transition can be a no current change transition, a cathodic current increase transition, a cathodic current decrease transition, a cathodic current decrease/anodic current increase transition, an anodic current increase transition, an anodic current decrease transition, and an anodic current decrease/cathodic current increase transition.

In order to understand how the heuristic rules can be applied using electrical current transitions between the immediate previously defined electrode configuration and the final electrode configuration, an exemplary set of heuristic rules will now be described with respect to FIG. 15B.

For ease of reference, as illustrated in box 402, specific electrical current transitions are assigned numeric designators 1-6, and in particular, 0=no current change; 1=cathodic current increase; 2=cathodic current decrease; 3=cathodic current decrease/anodic current increase; 4=anodic current increase; 5=anodic current decrease; and 6=anodic current decrease/cathodic current increase. These designators will be exclusively employed in the following discussion. Thus, a transition from one electrode configuration to a second electrode configuration can be characterized completely by identifying the current changes for each electrode.

Moreover, it has been noted that certain combinations of current transitions for a pair of electrodes naturally occur when transitioning current (i.e., when current is changed for one electrode to effect a specific current transition, the current is naturally changed for another electrode to effect a different current transition). Such combinations are termed "Natural Direction Combinations," and are set out in box 404. As can be seen there, a first natural combination is the combination of transitions 1 and 2; that is, an increase in cathodic current for one electrode coupled with a decrease in cathodic current for the other electrode. A second natural combination is the combination of transitions 1 and 3; that is, an increase in cathode current for one electrode coupled with an increase in cathodic current/decrease in anodic current for the other electrode. A third natural combination is the combination of transitions of 4 and 5; that is, an increase in anodic current for one electrode coupled with a decrease in anodic current for the other electrode. A fourth natural combination is the combination of transitions of 4 and 6; that is, an increase in anodic current for one electrode coupled with a decrease in anodic current/increase in cathodic current for the other electrode.

The heuristic rules embodied in FIG. 15B can generally be described as follows. The decision blocks 406, 408, 416, and 422 inquire into the nature of the current transitions required between the previously defined intermediate electrode configuration and the final electrode configuration, and action blocks 410, 412, 414, 418, 420, 424, and 426 govern the current transitions to be achieved based on these inquiries, and subject to the maximum limits discussed above.

The first inquiry is whether all of the electrodes either require a transition 3 or a transition 6 (step 406). If not all of the electrodes either require a transition 3 or a transition 6, it is determined whether any of the four natural direction combinations shown in box 604 exist (step 408).

If any of the four natural direction combinations exists, current is shifted in accordance with the natural direction combinations in the following order. If a natural combination of transitions 4 and 6 exists, anodic current is shifted from the electrode having the transition 6 to the electrode having the transition 4 (essentially attempting to eliminate the transition 6 from the electrode configuration) (step 410). If a natural combination of transitions 1 and 3 exists, cathodic current is shifted from the electrode having the transition 3 to the electrode having the transition 1 (essentially attempting to eliminate the transition 3) (step 412). If any other natural combination of transitions exists, cathodic current is shifted from the electrode having the transition 2 to the electrode having the transition 1 in the case where the natural combination of transitions 1 and 2 exists, and anodic current is shifted from the electrode having the transition 5 to the electrode having the transition 4 in the case where the natural combination of transitions 4 and 5 exists (step 414).

If none of the four natural direction combinations exists, it is determined whether there exists an electrode having a transition 6, and another electrode having either a transition 0 or a transition 5 (step 416). If so, anodic current is shifted from the electrode having the transition 6 to the electrode having the transition 0 or 5 (essentially converting the transition 6 to the transition 1) (step 418). If not, cathodic current is shifted from an electrode having a transition 3 to an electrode having a transition 0 or an electrode having a transition 2 (essentially converting the transition 3 to the transition 4) (step 420).

If all of the electrodes either require a transition 3 or a transition 6 at step 608, it determined whether there exists multiple electrodes having a transition 6 (step 422). If so, anodic current is shifted from the electrode having the greatest cathodic current for the final electrode configuration to another electrode (essentially converting a transition 6 to a transition 1) (step 424). If not, cathodic current is shifted from any cathodic electrode in the previous intermediate electrode configuration to the electrode having the greatest cathodic current in the previous intermediate electrode configuration (essentially converting a transition 3 to a transition 4) (step 426).

The set of heuristic rules embodied in FIGS. 15A and 15B can thus be stated as follows:

Rule 1: Determine whether all of the electrodes either have a cathodic current decrease/anodic current increase transition (transition 3) or an anodic current decrease/cathodic current decrease transition (transition 6), and if not, go to Rules 2-7, and if so, go to Rules 8-9.

Rule 2: Determine whether a first electrode pairing exists, having a cathodic current increase transition (transition 1) and a cathodic current decrease transition (transition 2). If so, shift cathodic current from the electrode having the cathodic current decrease transition (transition 2) to the electrode having the cathodic current increase transition (transition 1).

Rule 3: Determine whether a second electrode pairing exists having a cathodic current increase transition (transition 1) and a cathodic current decrease/anodic current increase transition (transition 3). If so, shift, cathodic current from the electrode having the cathodic current decrease/anodic current increase transition (transition 3) to the electrode having the cathodic current increase transition (transition 1).

Rule 4: Determine whether a third electrode pairing exists having an anodic current increase transition (transition 4) and an anodic current decrease transition (transition 5). If so, shift anodic current from the electrode having the anodic current decrease transition (transition 5) to the electrode having the anodic current increase transition (transition 4).

Rule 5: Determine whether a fourth electrode pairing having an anodic current increase transition (transition 4) and an anodic current decrease/cathodic current increase transition (transition 6). If so, shift, anodic current from the electrode having the anodic current decrease/cathodic current increase transition (transition 6) to the electrode having the anodic current increase transition (transition 40.

Rule 6: If none of the first through fourth electrode pairings exist, determine whether a first electrode exists having an anodic current decrease/cathodic current increase transition (transition 6) and whether a second electrode exists having either a no current change transition (transition 0) or an anodic current decrease transition (transition 5). If so, shift anodic current from the first electrode to the second electrode.

Rule 7: If either the first electrode or the second electrode does not exist, shift cathodic current from an electrode having a cathodic current decrease/anodic current increase transition to an electrode having either a no current change transition or a cathodic current decrease transition.

Rule 8: If all of the electrodes either have a cathodic current decrease/anodic current increase transition (transition 3) or an anodic current decrease/cathodic current increase transition (transition 6), and if there exists multiple electrodes each having an anodic current decrease/cathodic current increase transition (transition 6), determine which one of the multiple electrodes has the greatest cathodic current for the final electrode configuration, and shift anodic current from the one electrode to another electrode.

Rule 9: If the multiple electrodes do not exist, determine one electrode having the greatest cathodic current for the previous intermediate electrode configuration, and shift cathodic current from any electrode having cathodic current for the previous intermediate electrode configuration to the one electrode.

It will be understood that the application of heuristic rules, and the heuristic rules themselves, set out in the discussion above, are exemplary in nature. The empirical nature of the heuristic rules themselves suggests that further investigation could result in different rules, changes in the substantive nature of the rules themselves cannot affect the scope of the invention set out and claimed herein.

Figure 16:
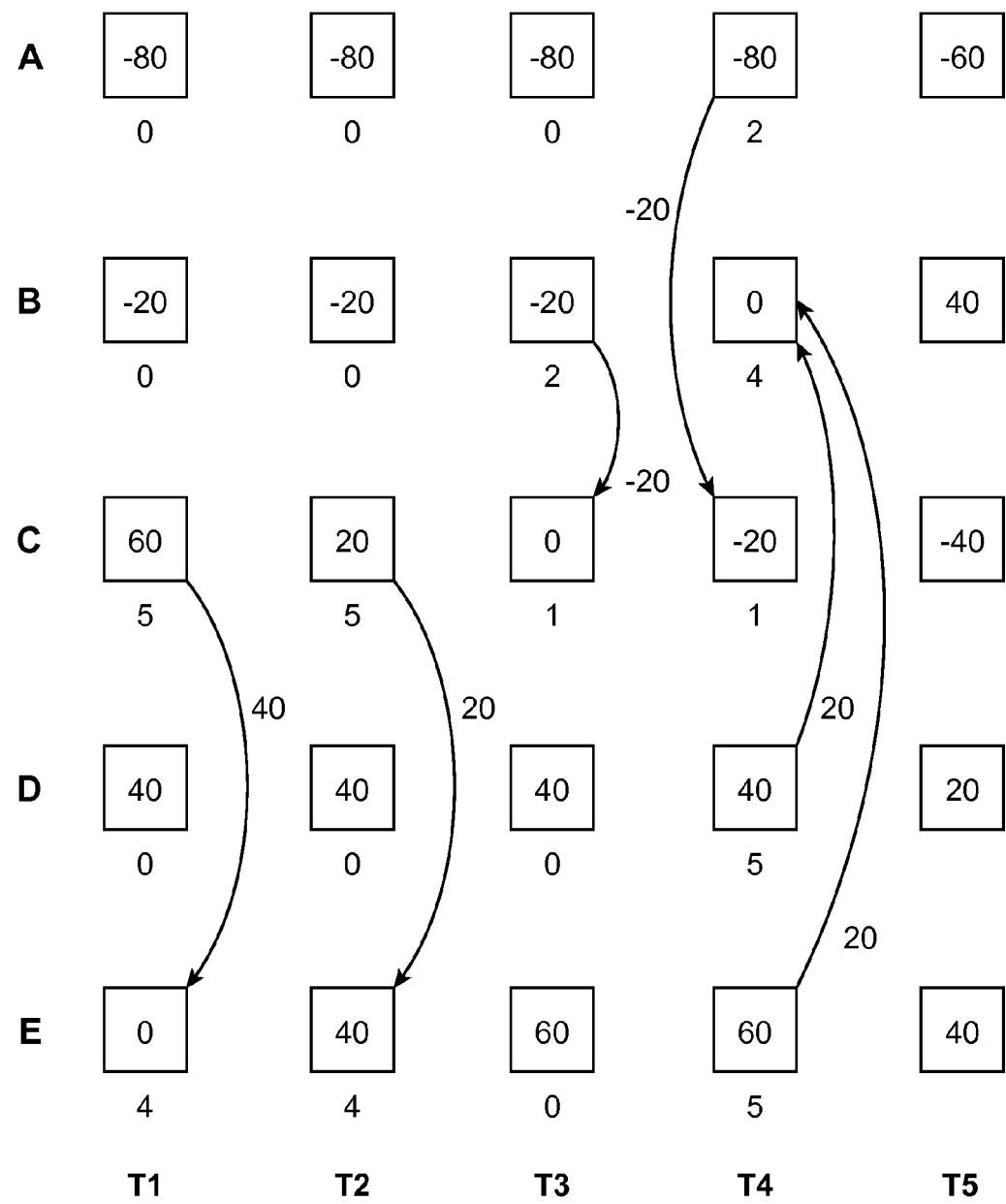
FIG. 16 is a schematic illustrating the intermediate current transitions performed by the heuristic rules illustrated in FIG. 15B to transition between one exemplary set of initial and final electrode configurations.

Referring now to FIG. 16, an example will now be discussed, employing the set of heuristic rules set out above. The diagram illustrates transitions between electrode configurations for a set of five electrodes, A-E, at five successive times T1-T5. Arrows represent shifts of fractionalized current from one electrode to another electrode, and numbers beside the arrow represent magnitude of change in the fractionalized current. Each intermediate electrode configuration becomes the becomes the starting point for the next intermediate electrode configuration. The numbers below each electrode box correspond to the current transition (specified in box 402 of FIG. 15B) required for that electrode to make the transition from an intermediate electrode configuration to the final electrode configuration. Here, a change in fractional current on any specific electrode (whether cathodic or anodic) is 40 percentage points.

Rules 1 and 4 are implemented for the intermediate electrode configuration at time T1, where not all of the electrodes have transitions 3 and 6, and there is a natural direction combination in that electrode C has 60% of the anodic current and a required transition 6 to make electrode C have 40% of the cathodic current in the final electrode configuration at time T5, and electrode E has 0% current and a required transition 4 to make electrode E have 40% of the anodic current in the final electrode configuration at time T5. In this case, 40% of the anodic current is shifted from electrode C to electrode E, resulting in an intermediate electrode configuration at time T2 where electrodes C and E respectively now have anodic currents of 20% and 40%. There are no other natural direction combinations for the intermediate electrode configuration at time T1.

Rules 1 and 6 are implemented for the intermediate electrode configuration at time T2, where not all of the electrodes have transitions 3 and 6, there are no natural direction combinations, and electrode C has 20% of the anodic current and a required transition 6 to make electrode C have 40% of the cathodic current in the final electrode configuration at time T5, and electrode E has 40% of the anodic current and a required transition 0 to make electrode E have 40% of the anodic current in the final electrode configuration at time T5. In this case, 20% of the anodic current is shifted from electrode C to electrode E, resulting in an intermediate electrode configuration at time T3 where electrodes C and E respectively now have a current of 0% and an anodic current of 60%.

Rules 1 and 3 are implemented for the intermediate electrode configuration at time T3, where not all of the electrodes have transitions 3 and 6, and there is a natural direction combination in that electrode B has 20% of the cathodic current and a required transition 3 to make electrode B have 40% of the anodic current in the final electrode configuration at time T5, and electrode C has 0% current and a required transition 1 to make electrode C have 40% of the cathodic current in the final electrode configuration at time T5. In this case, 20% of the cathodic current is shifted from electrode B to electrode C, resulting in an intermediate electrode configuration at time T4 where electrodes B and C respectively now have a current of 0% and a cathodic current of 20%. There are no other natural direction combinations for the intermediate electrode configuration at time T1.

Rules 1, 2, and 4 are implemented for the intermediate electrode configuration at time T4, where not all of the electrodes have transitions 3 and 6, and there is a first natural direction combination in that electrode A has 80% of the cathodic current and a required transition 2 to make electrode A have 60% of the cathodic current in the final electrode configuration at time T5, and electrode C has 20% of the cathodic current and a required transition 1 to make electrode C have 40% of the cathodic current in the final electrode configuration at time T5, and a second natural direction combination in that electrode B has 0% current and a required transition of 4 to make electrode B have 40% of the anodic current, electrode D has 40% of the anodic current and a required transition of 5 to make electrode D have 20% of the anodic current in the final electrode configuration at time T5, and electrode E has 60% of the anodic current and a required transition of 5 to make electrode E have 40% of the anodic current in the final electrode configuration. In this case, 20% of the cathodic current is shifted from electrode A to electrode C, resulting in the desired final electrode configuration at time T5 where electrodes A and C respectively have a cathodic current of 60% and a cathodic current of 40%, and 20% of the anodic current is shifted from electrode D to electrode B, and 20% of the anodic current is shifted from electrode E to electrode B, resulting in the desired final electrode configuration at time T5 where electrodes B, D, and E respective have an anodic current of 40%, an anodic current of 20%, and an anodic current of 40%.

Figures 1, 17:
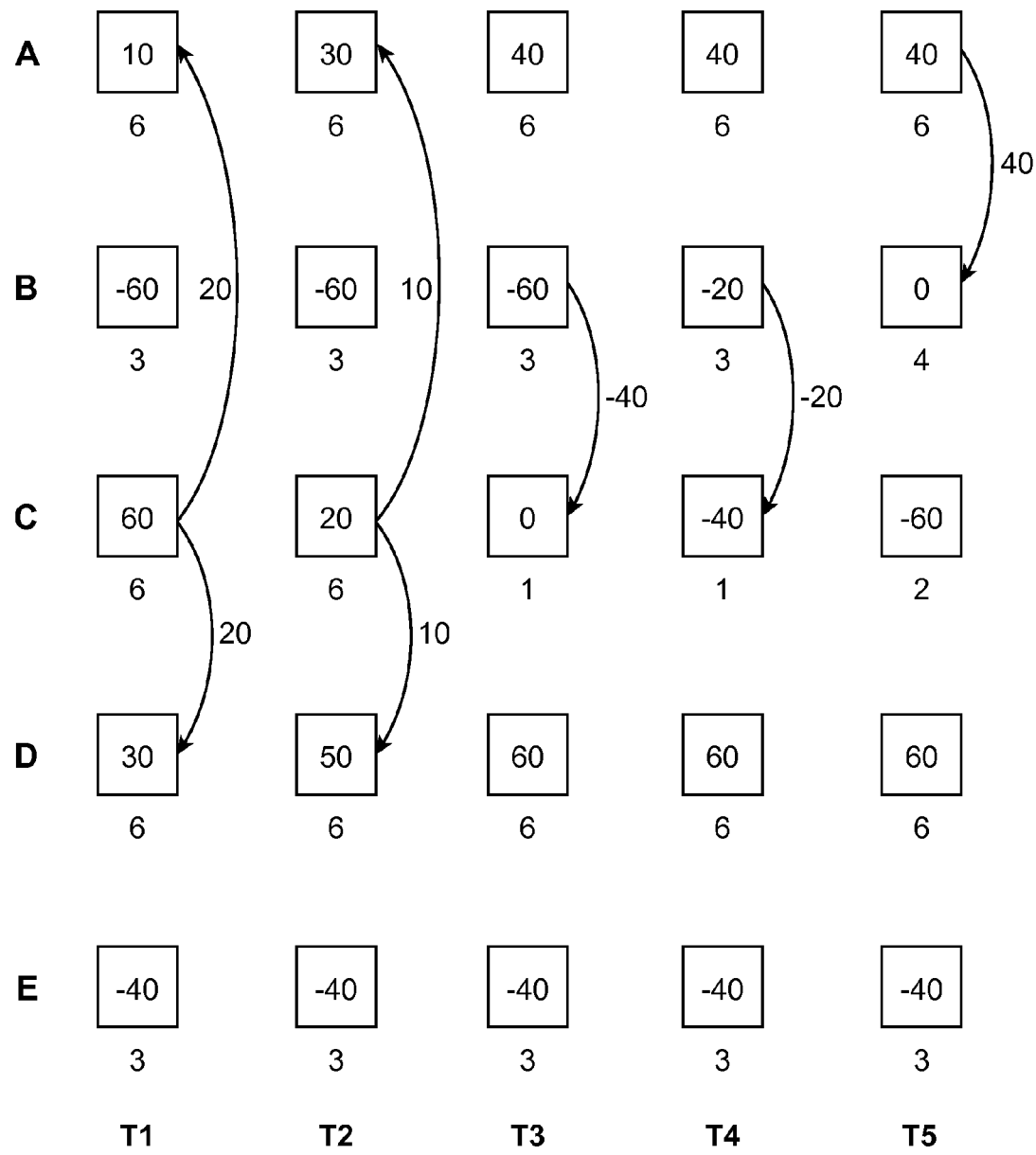
FIG. 17 (17-1-17-2) is a schematic illustrating the intermediate current transitions performed by the heuristic rules illustrated in FIG. 15B to transition between another exemplary set of initial and final electrode configurations.
Figures 2, 17:
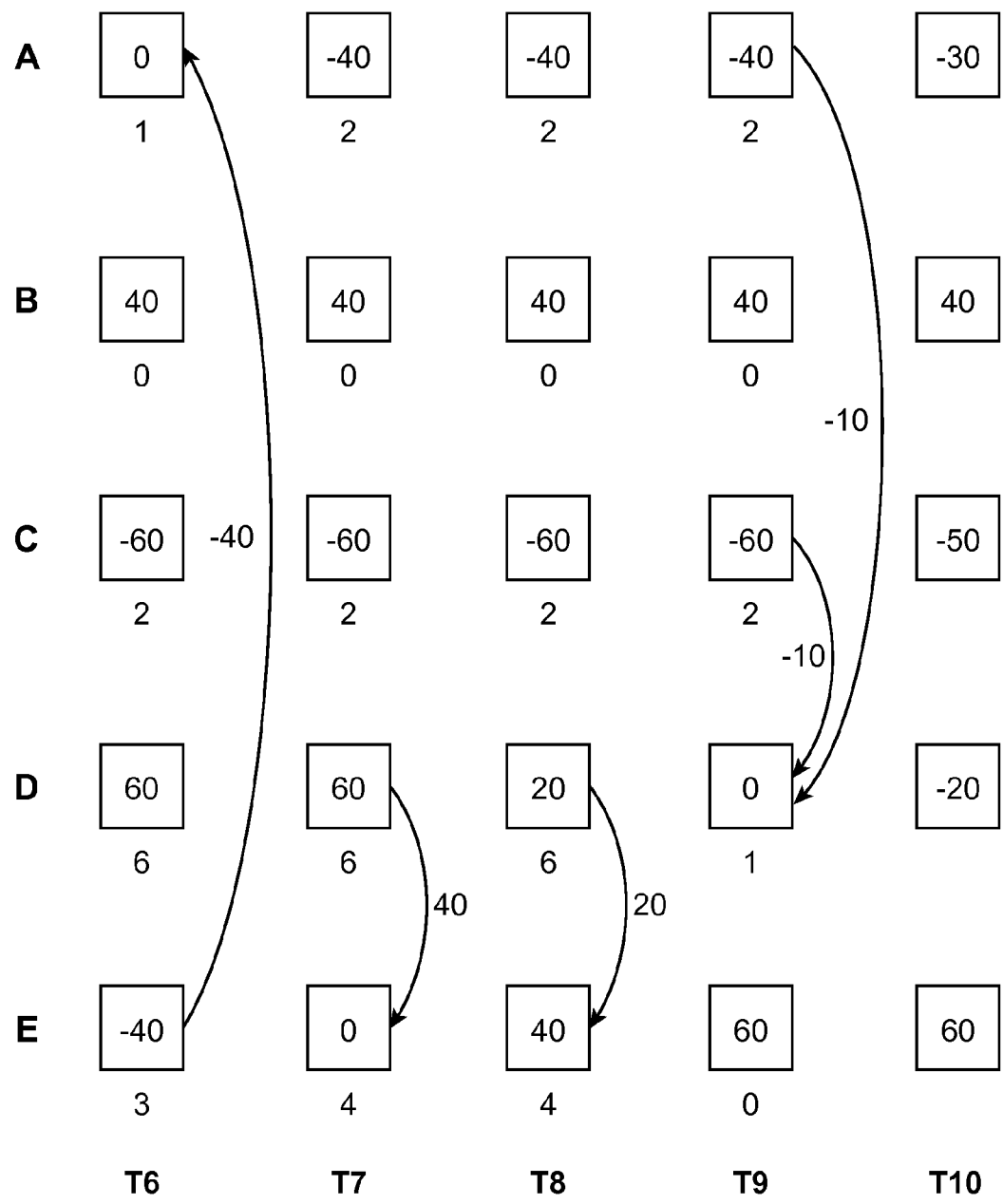

With reference to FIG. 17, in another example, rules 1 and 8 are implemented for the intermediate electrode configuration at time T1, where all of the electrodes have transitions 3 and 6, there are multiple electrodes with transitions 6, and all of the anodic current must be shifted from the electrode having the largest cathodic current for the final electrode configuration. In this case, electrode C has the greatest cathodic current for the final electrode configuration at 50%, and thus, 20% of the anodic current is shifted from electrode C to electrode A, and 20% of the anodic current is shifted from electrode C to electrode D, resulting in an intermediate electrode configuration at time T2 where electrodes A, C, and D respectively now have anodic currents of 30%, 20%, and 50%. Notably, since the maximum current that can be shifted to or from any individual electrode is 40% for each transition, and electrode C had an anodic current of 60% at time T1, an additional 20% of the anodic current must be shifted from electrode C, in which case, 10% of the anodic current is shifted from electrode C to electrode A, and 10% of the anodic current is shifted from electrode C to electrode D, resulting in an intermediate electrode configuration at time T3 where electrodes A, C, and D respectively now have anodic currents of 40%, 0%, and 60%. For the remaining intermediate electrode configurations at times T3-T9, rules 2-5 are implemented to shift current between natural direction combinations, resulting in the final electrode configuration at time T10.

Figures 1, 18:
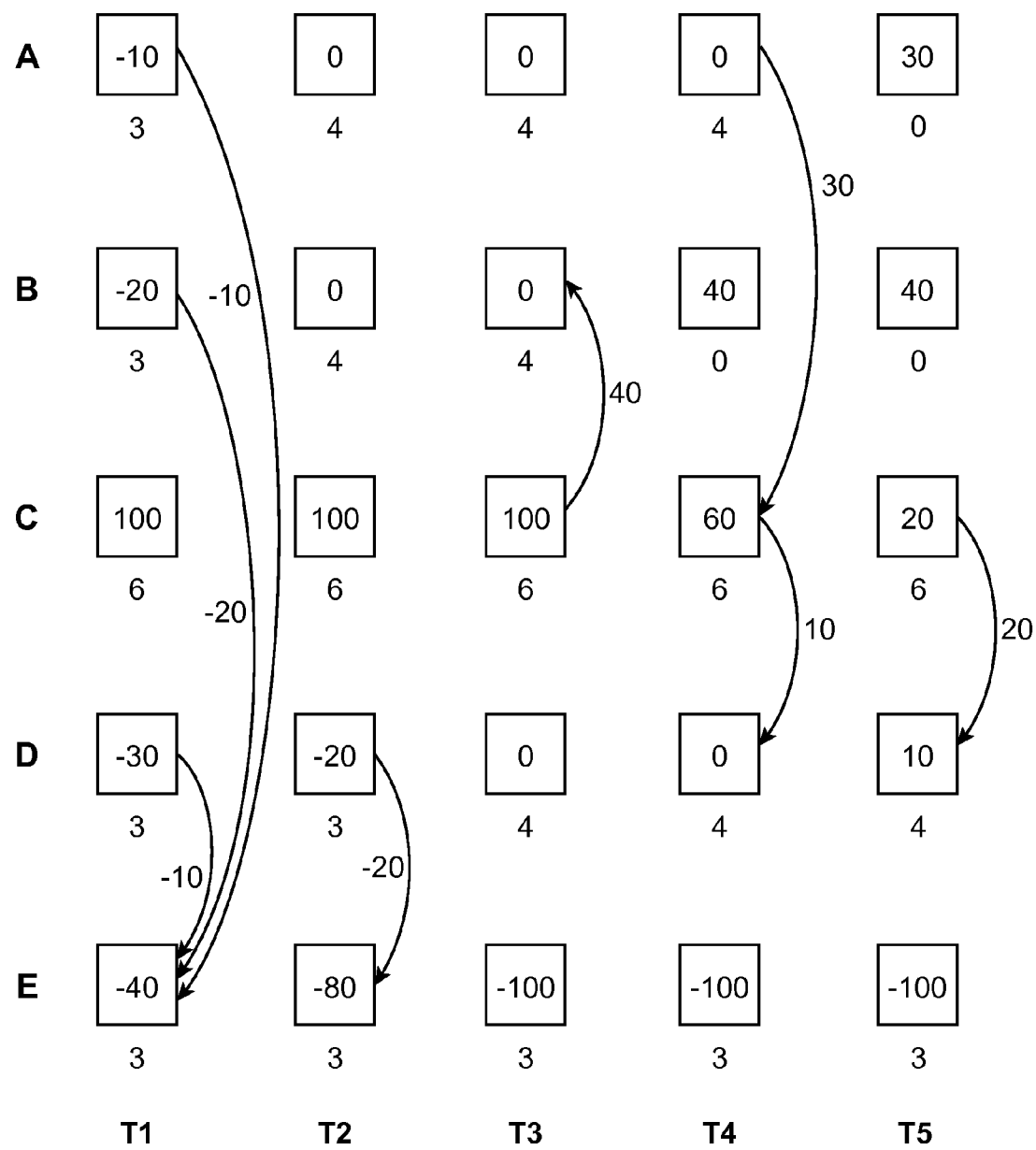
FIG. 18 (18-1-18-2) is a schematic illustrating the intermediate current transitions performed by the heuristic rules illustrated in FIG. 15B to transition between still another exemplary set of initial and final electrode configurations.
Figures 2, 18:
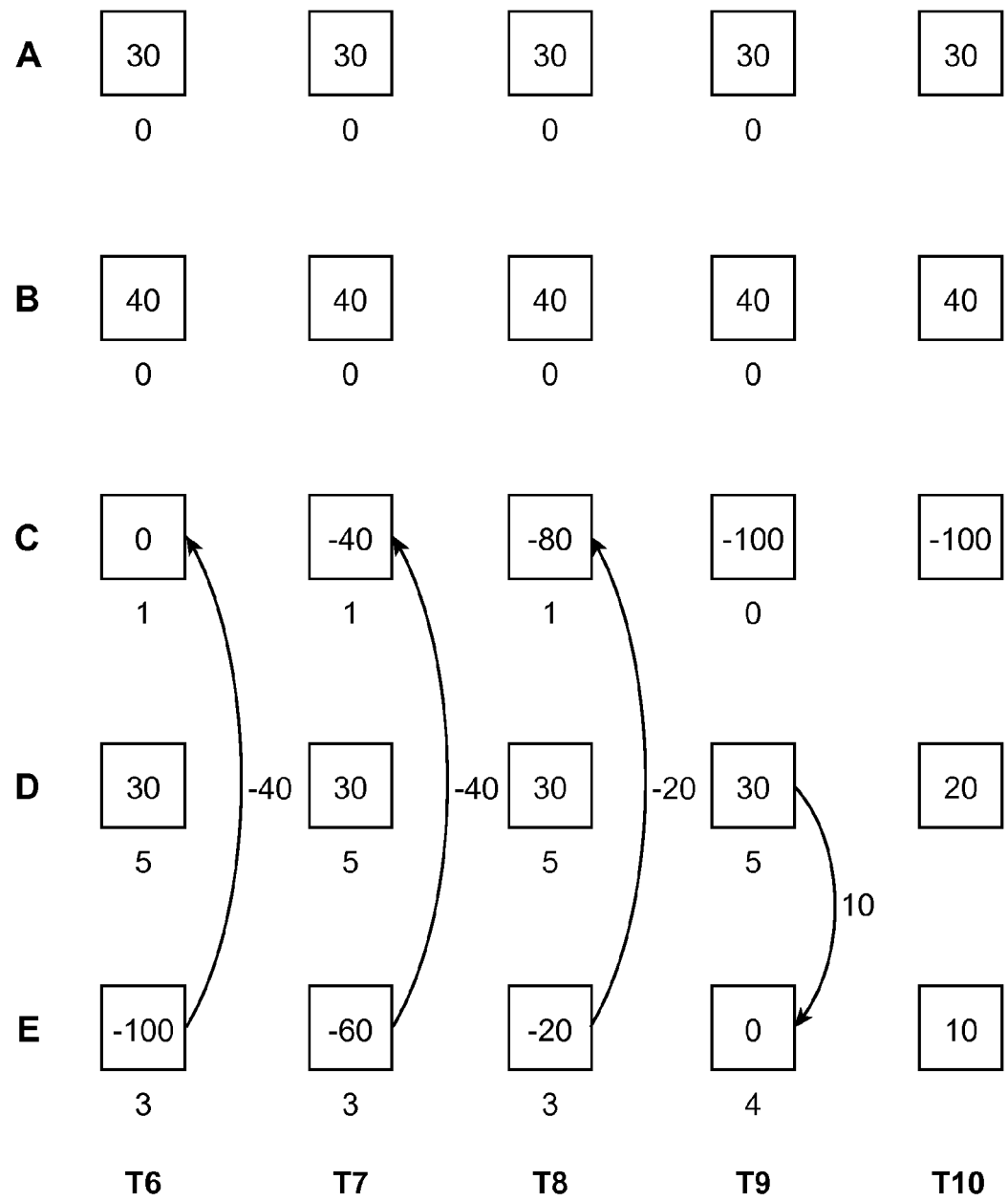

With reference to FIG. 18, in still another example, rules 1 and 9 are implemented for the intermediate electrode configuration at time T1, where all of the electrodes have transitions 3 and 6, there is only one electrode with a transition 6, all cathodic current must be consolidated to the electrode having the largest cathodic current. In this case, electrode E has the greatest cathodic current for the intermediate electrode configuration at time T1 at 40%, and thus, 10% of the cathodic current is shifted from electrode A to electrode E, 20% of the cathodic current is shifted from electrode B to electrode E, and 10% of the cathodic current is shifted from electrode D to electrode E, resulting in an intermediate electrode configuration at time T2 where electrodes A, B, D, and E respectively now have cathodic currents of 0%, 0%, 20%, and 80%. Notably, since the maximum current that can be shifted to or from any individual electrode is 40% for each transition, and 60% of the cathodic current must be shifted to electrode E to consolidate all of the cathodic current in one electrode, an additional 20% of the cathodic current must be shifted to electrode E1, in which case, 20% of the remaining current on electrode D is shifted to electrode E, resulting in an intermediate electrode configuration at time T3 where electrodes D and E respectively now have cathodic currents of 0% and 100%, thereby effecting full consolidation of the cathodic current in one electrode. For the remaining intermediate electrode configurations at times T3-T9, rules 2-5 are implemented to shift current between natural direction combinations, resulting in the final electrode configuration at time T10.

Figures 1, 19:
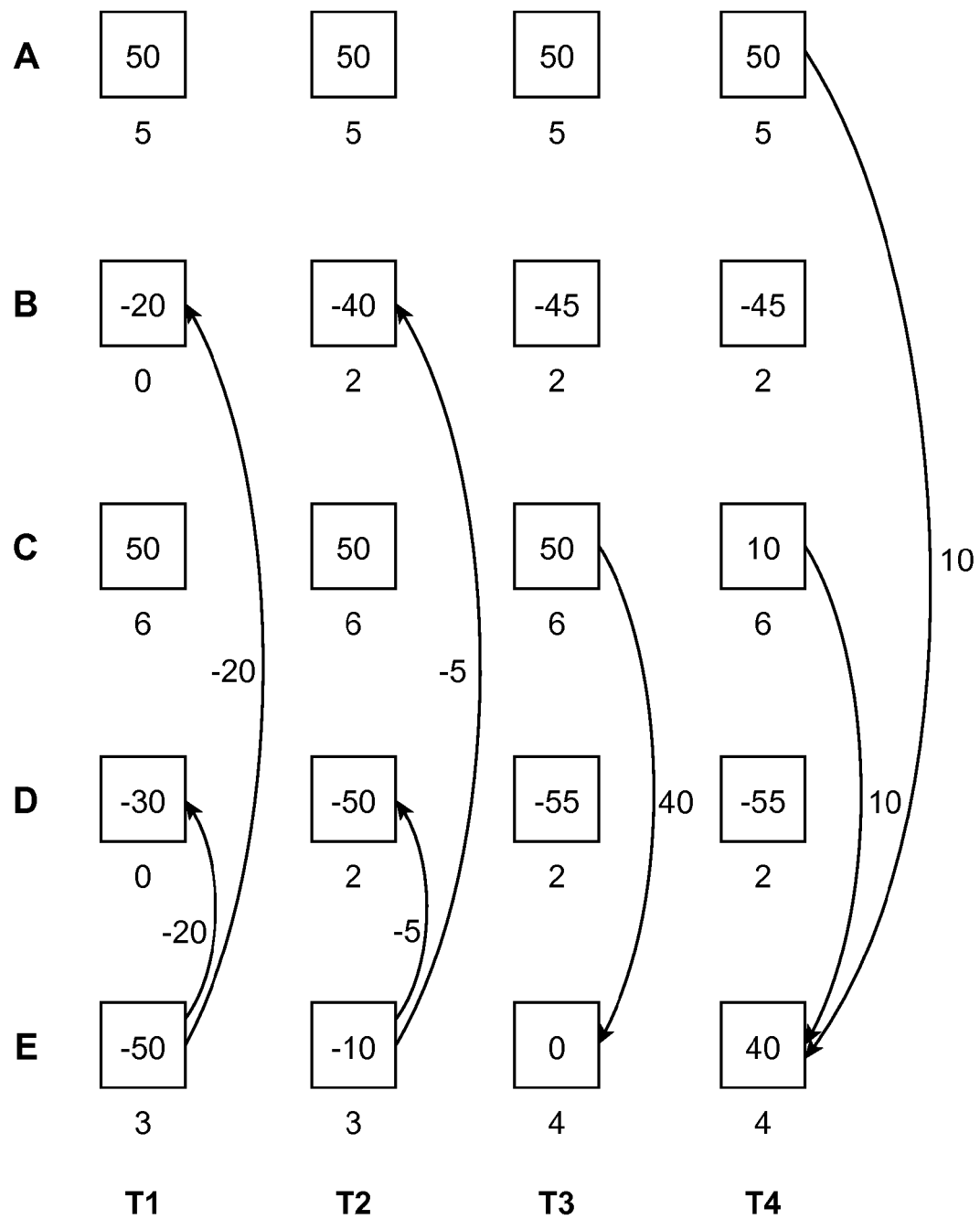
FIG. 19 (19-1-19-2) is a schematic illustrating the intermediate current transitions performed by the heuristic rules illustrated in FIG. 15B to transition between yet another exemplary set of initial and final electrode configurations.
Figures 2, 19:
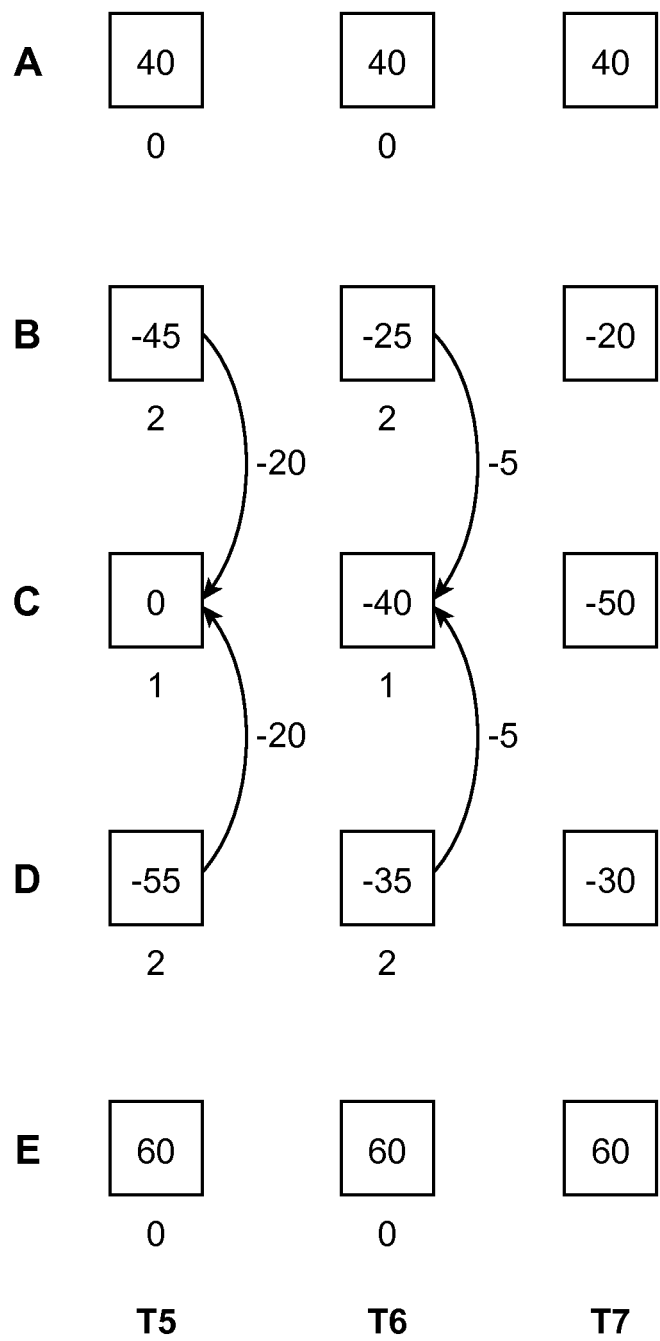
Figure 17:
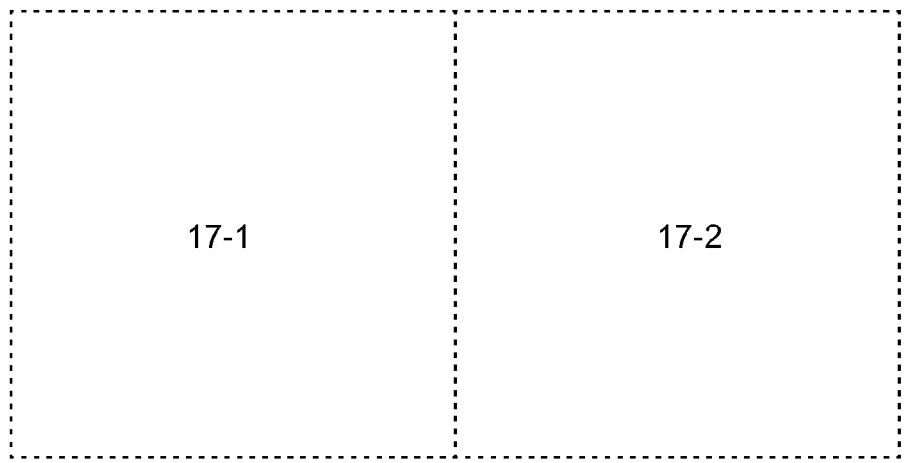
Figure 18:
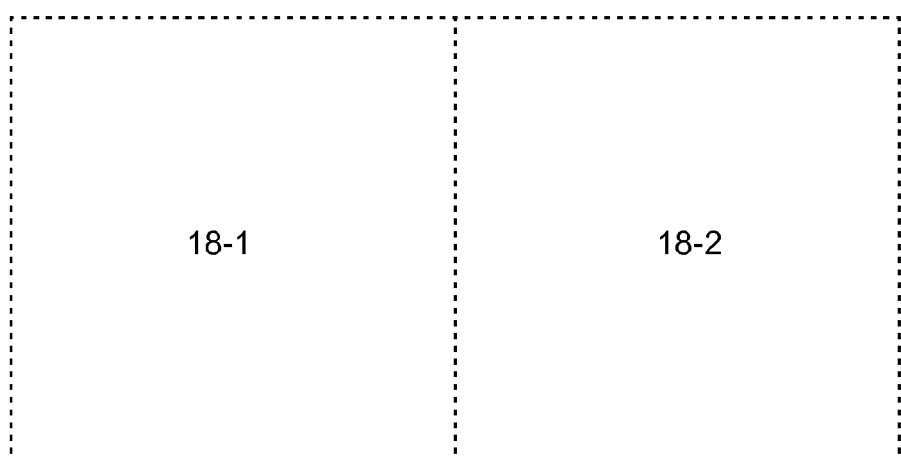
Figure 19:
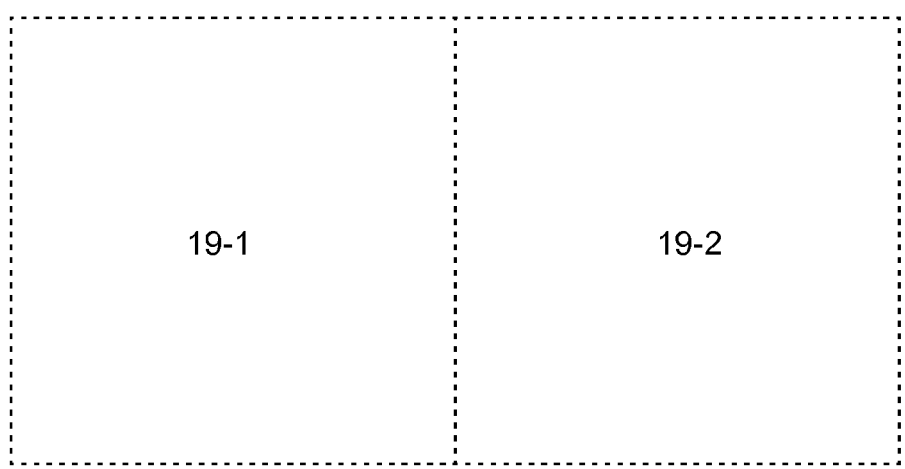

With reference to FIG. 19, in another example, rules 1, 6, and 7 are implemented for the intermediate electrode configuration at time T1, where not all of the electrodes have transitions 3 and 6, there are no natural direction combinations, and there are no electrodes with transitions of 0 or 5, and the cathodic current must be shifted from the electrode having a transition of 3 to the electrodes with transitions of 0 or 2. In this case, electrode E has a transition of 3, and electrodes B and D have transitions of 0, and thus, 20% of the cathodic current is shifted from electrode E to electrode B, and 20% of the cathodic current is shifted from electrode E to electrode D, resulting in an intermediate electrode configuration at time T2 where electrodes B, D, and E respectively now have cathodic currents 20%, 30%, and 50%. Notably, since the maximum current that can be shifted to or from any individual electrode is 40% for each transition, and electrode E had a cathodic current of 50% at time T1, an additional 10% of the cathodic current must be shifted from electrode C, in which case, 5% of the cathodic current is shifted from electrode E to electrode B, and 5% of the cathodic current is shifted from electrode E to electrode B, resulting in an intermediate electrode configuration at time T3 where electrodes B, D, and E respectively now have cathodic currents of 40%, 50%, and 10%. For the remaining intermediate electrode configurations at times T3-T6, rules 2-5 are implemented to shift current between natural direction combinations, resulting in the final electrode configuration at time T7.

Although particular embodiments of the present disclosure have been shown and described, it will be understood that it is not intended to limit the present disclosure to the preferred embodiments, and it will be obvious to those skilled in the art that various changes and modifications may be made without departing from the spirit and scope of the present disclosure. Thus, the present disclosure are intended to cover alternatives, modifications, and equivalents, which may be included within the spirit and scope of the present disclosure as defined by the claims.

What is claimed is:

1. A system for an electrical neurostimulator coupled to a plurality of electrodes, comprising:
   a user interface configured for receiving a user input; and
   a controller/processor configured for (a) defining an immediate virtual multipole, (b) defining an immediate electrode configuration that emulates the immediate virtual multipole, (c) defining a new virtual multipole by changing a parameter of the immediate virtual multipole by a step size in response to the user input, (d) defining a new electrode configuration that emulates the new virtual multipole, (e) computing a difference value as a function of the immediate virtual multipole and the new virtual multipole, (f) comparing the difference value to a limit value, (g) decreasing the absolute value of the step size when the difference value exceeds the limit value to create a new step size, and (h) repeating steps (c)-(f) for the new step size.

2. The system of claim 1, further comprising (g) instructing the electrical neurostimulator to convey electrical energy to the plurality of electrodes in accordance with the new electrode configuration after steps (c)-(f) have been repeated.

3. The system of claim 1, wherein the controller/processor is configured for (g) not instructing the electrical neurostimulation to convey electrical energy to the plurality of electrodes in accordance with the new electrode configuration before steps (c)-(f) have been repeated.

4. The system of claim 1, wherein the controller/processor is configured for (c) defining the new virtual multipole by changing at least one other parameter of the immediate virtual multipole by another step size, and (g) decreasing the absolute value of the other step size to create another new step size for the other parameter when a difference value for the immediate and new virtual multipole exceeds a limit value, and repeating steps (c)-(f) for the new step size and the other new step size.

5. The system of claim 1, wherein the parameter comprises one of a location, focus, and upper anode percentage of the immediate virtual multipole.

6. The system of claim 1, wherein the step size is one of a positive value and a negative value.

7. The system of claim 1, wherein the controller/processor is configured for (e) computing another difference value as another function of the immediate virtual multipole and the new virtual multipole, (f) comparing the other difference value to another limit value, and (g) decreasing the absolute value of the step size when the other difference value exceeds the other limit value to create the new step size.

8. The system of claim 1, wherein the difference value is a function of the immediate electrode configuration and the new electrode configuration.

9. The system of claim 8, wherein the difference value comprises one of a change in a cathodic current on an individual one of the electrodes, a change in an anodic current on an individual one of the electrodes, a total change in cathodic current on the electrodes, and a total change in anodic current on the electrodes.

10. The system of claim 1, wherein the difference value is a function of one of an electrical field, absolute potential, current density, an activating function, and a total net driving function that is derived from the immediate virtual multipole and the new virtual multipole.

11. The system of claim 1, wherein the difference value is a displacement between one pole of the immediate virtual multipole and a corresponding pole of the new virtual multipole.

12. The system of claim 1, further comprising telemetry circuitry configured for communicating with the electrical neurostimulator, wherein the controller/processor is further configured for instructing the electrical neurostimulator via the telemetry circuitry to convey electrical energy to the plurality of electrodes in accordance with the immediate electrode configuration.

13. The system of claim 1, wherein the immediate and new electrode configurations are respectively immediate and new fractionalized combinations.

14. The system of claim 1, further comprising a housing containing the user interface and the controller/processor.

15. A method of providing therapy to a patient using a plurality of electrodes, comprising:
(a) defining an immediate virtual multipole;
(b) defining an immediate electrode configuration that emulates the immediate virtual multipole;
(c) receiving an input from a user;
(d) defining a new virtual multipole in response to the user input by changing a parameter of the immediate virtual multipole by a step size;
(e) defining a new electrode configuration that emulates the new virtual multipole;
(f) computing a difference value as a function of the immediate virtual multipole and the new virtual multipole;
(g) comparing the difference value to a limit value;
(h) decreasing the absolute value of the step size when the difference value exceeds the limit value to create a new step size, and repeating steps (c)-(g) for the new step size.

16. The method of claim 15, further comprising (i) conveying electrical energy to the plurality of electrodes in accordance with the new electrode configuration after steps (c)-(g) have been repeated.

17. The method of claim 15, further comprising (i) not instructing the electrical neurostimulation to convey electrical energy to the plurality of electrodes in accordance with the new electrode configuration before steps (c)-(g) have been repeated.

18. The method of claim 15, wherein:
(d) the new virtual multipole is defined by changing another parameter of the immediate virtual multipole by another step size; and
(h) the absolute value of the other step size is decreased to create another new step size, and steps (c)-(g) are repeated for the new step size and the other new step size if the difference value exceeds the limit value.

19. The method of claim 15, wherein the parameter comprises one of a location, focus, and upper anode percentage of the immediate virtual multipole.

20. The method of claim 15, wherein the step size is one of a positive value and a negative value.

21. The method of claim 15, wherein:
(f) another difference value is computed as another function of the immediate virtual multipole and the new virtual multipole;
(g) the other difference value is compared to another limit value; and
(h) the absolute value of the step size when the other difference value exceeds the other limit value is decreased to create the new step size.

22. The method of claim 15, wherein the difference value is a function of the immediate electrode configuration and the new electrode configuration.

23. The method of claim 22, wherein the difference value comprises one of a change in a cathodic current on an individual one of the electrodes, a change in an anodic current on an individual one of the electrodes, a total change in cathodic current on the electrodes, and a total change in anodic current on the electrodes.

24. The method of claim 15, wherein the difference value is a function of one of an electrical field, absolute potential, current density, an activating function, and a total net driving function that is derived from the immediate virtual multipole and the new virtual multipole.

25. The method of claim 15, wherein the difference value is a displacement between one pole of the immediate virtual multipole and a corresponding pole of the new virtual multipole.

26. The method of claim 15, further comprising conveying electrical energy to the plurality of electrodes in accordance with the immediate electrode configuration.

27. The method of claim 15, wherein the immediate and new electrode configurations are respectively immediate and new fractionalized combinations.

* * * * *